US012767702B2

(12) United States Patent
Zhang et al.

(10) Patent No.: US 12,767,702 B2
(45) Date of Patent: Oct. 20, 2026

(54) ANTI-VARICELLA-ZOSTER VIRUS ANTIBODY AND USE THEREOF

(71) Applicants: Beijing Wisdomab Biotechnology Co., Ltd., Beijing (CN); GENRIX (Shanghai) Biopharmaceutical Co., Ltd., Shanghai (CN); Chongqing Genrix Biopharmaceutical Co., Ltd., Chongqing (CN)

(72) Inventors: Xueping Zhang, Beijing (CN); Zhigang Liu, Beijing (CN); Xiaowei Zhou, Beijing (CN); Xiaobo Hao, Beijing (CN); Junjie Hu, Beijing (CN); Yulan Liu, Beijing (CN)

(73) Assignees: Beijing Wisdomab Biotechnology Co., Ltd, Beijing (CN); GENRIX (Shanghai) Biopharmaceutical Co., Ltd., Shanghai (CN); Chongqing Genrix Biopharmaceutical Co., Ltd., Chongqing (CN)

( * ) Notice: Subject to any disclaimer, the term of this patent is extended or adjusted under 35 U.S.C. 154(b) by 486 days.

(21) Appl. No.: 18/281,207

(22) PCT Filed: Jan. 21, 2022

(86) PCT No.: PCT/CN2022/073199

§ 371 (c)(1),
(2) Date: Sep. 8, 2023

(87) PCT Pub. No.: WO2022/188565

PCT Pub. Date: Sep. 15, 2022

(65) Prior Publication Data

US 2024/0166725 A1 May 23, 2024

(30) Foreign Application Priority Data

Mar. 10, 2021 (CN) ......................... 202110259834.4

(51) Int. Cl.

| | |
|---|---|
| ***C07K 16/085*** | (2026.01) |
| ***A61K 39/00*** | (2006.01) |
| ***A61P 31/22*** | (2006.01) |

(52) U.S. Cl.

CPC ............ *C07K 16/088* (2013.01); *A61P 31/22* (2018.01); *A61K 2039/505* (2013.01); *C07K 2317/565* (2013.01); *C07K 2317/732* (2013.01); *C07K 2317/76* (2013.01)

(58) Field of Classification Search

CPC ............ C07K 16/088; C07K 2317/565; C07K 2317/732; C07K 2317/76; C07K 2317/21; C07K 2317/622; C07K 2317/92; C07K 2317/56; A61P 31/22; A61K 2039/505; A61K 39/42; A61K 47/64

See application file for complete search history.

(56) References Cited

U.S. PATENT DOCUMENTS

| | | | |
|---|---|---|---|
| 4,816,567 | A | 3/1989 | Cabilly |
| 5,710,248 | A | 1/1998 | Grose |
| 2010/0074906 | A1 | 3/2010 | Burioni |
| 2017/0327571 | A1 | 11/2017 | Liu |
| 2019/0328867 | A1 | 10/2019 | Ahmed |
| 2019/0367561 | A1 | 12/2019 | Cui |

FOREIGN PATENT DOCUMENTS

| | | | |
|---|---|---|---|
| CN | 101663318 | A | 3/2010 |
| CN | 105669838 | A | 6/2016 |
| CN | 106279378 | A | 1/2017 |
| CN | 105315371 | B | 5/2018 |
| CN | 110231481 | A | 9/2019 |
| CN | 111579789 | A | 8/2020 |
| WO | 1991016448 | A1 | 10/1991 |
| WO | WO 9504080 | A1 | 2/1995 |
| WO | WO 9531546 | A1 | 11/1995 |

OTHER PUBLICATIONS

MMWR Recommendations and Reports Jul. 12, 1996 / 45(RR11);1-25 (Year: 1996).*

Agostini et al. "Immunoglobulins in the treatment of herpes zoster." PubMed, Retrieved from the Internet at <https://pubmed.ncbi.nlm.nih.gov/1468193/> (1992) [Abstract].

Brunell et al. "Passive immunization against varicella-zoster infections and other modes of therapy." Journal of Infectious Diseases 127.4: 415-423 (1973) [Abstract].

Suzuki et al. "Isolation of therapeutic human monoclonal antibodies for varicella-zoster virus and the effect of light chains on the neutralizing activity." Journal of medical virology 79.6: 852-862 (2007).

International Search Report and Written Opinion of International Searching Authority for International Patent Application No. PCT/CN2022/073199, mailed Mar. 29, 2022, with English language translation of Search Report (17 pages).

Cai, Linli et al.; "Preparation of Monoclonal Antibodies Against Major Capsid Protein Orf40 of Varicella-Zoster Virus and Its Preliminary Study"; Chinese journal of Immunology, vol. 35, No. 9, pp. 1095-1099; with English abstract; Dec. 31, 2019; DOI: 10.3969/j.issn.1000-484X.2019.09.014 (5 pages).

Birlea, M. et al.; "Human Anti-Varicella-Zoster Virus (VZV) Recombinant Monoclonal Antibody Produced after Zostavax Immunization Recognizes the gH/gL Complex and Neutralizes VZV Infection"; Journal of Virology, vol. 87, No. 1, pp. 415-421; Oct. 17, 2012 (7 pages).

(Continued)

*Primary Examiner* — Thomas J. Visone
*Assistant Examiner* — Cassandra Senn Grizer
(74) *Attorney, Agent, or Firm* — Nixon Peabody LLP; Bradley M. Taub; Nicole D. Kling

(57) ABSTRACT

Provided are an antibody against varicella-zoster virus, a nucleic acid molecule encoding the antibody, an expression vector comprising the nucleic acid molecule, a host cell comprising the nucleic acid molecule or the vector, a method for preparing and purifying the antibody, and the use of the antibody.

17 Claims, 2 Drawing Sheets

Specification includes a Sequence Listing.

(56) References Cited

OTHER PUBLICATIONS

Al-Lazikani, B. et al.; "Standard Conformations for the Canonical Structures of Immunoglobulins"; J. Mol. Biol., vol. 273, No. 4, pp. 927-948; Academic Press Limited; Aug. 6, 1997 (22 pages).
Martin, et al.; "Modeling antibody hypervariable loops: a combined algorithm"; Proc. Natl. Acad. Sci. USA, vol. 86, pp. 9268-9272; Dec. 1989 (5 pages).
Morrison, S. L. et al.; "Chimeric human antibody molecules: mouse antigen-binding domains with human constant region domains"; Proc. Natl. Acad. Sci. USA, vol. 81, No. 21, pp. 6851-6855; Nov. 1984 (5 pages).
Krebber, A. et al.; "Reliable cloning of functional antibody variable domains from hybridomas and spleen cell repertoires employing a reengineered phase display system"; J. Immunol. Methods, vol. 201, No. 1, pp. 35-55; accepted Sep. 25, 1996, published 1997 (21 pages).
Davison, A. J. et al.; "The Complete DNA Sequence of Varicella-Zoster Virus"; J. Gen. Virol., vol. 67, pp. 1759-1816; Apr. 23, 1986 (58 pages).
Davison, A. J. et al.; "New Common Nomenclature for Glycoprotein Genes of Varicella-Zoster Virus and Their Glycosylated Products"; J. Virol., vol. 57, No. 3, pp. 1195-1197; Mar. 1986 (3 pages).
Kapsenberk, J. G.; "Possible Antigenic Relationship Between Varicella/Zoster Virus and Herpes Simplex Virus"; Arch. Ges. Virusforsch, vol. 15, pp. 67-73; May 25, 1964 (7 pages).
Forghani, B. et al.; "Neutralization Epitrope of the Varicella-Zoster Virus gH:gL Glycoprotein Complex"; Virology, vol. 199, pp. 458-462; 1994 (5 pages).
Zhu, Z. et al.; "Infection of cells by varicella-zoster virus inhibition of viral entry by mannose 6-phosphate and heparin"; Proc. Natl. Acad. Sci. USA, vol. 92, pp. 3546-3550; Apr. 1995 (5 pages).
Chen, J. et al.; "Latent and lytic infection of isolated guinea pig enteric and dorsal root ganglia by varicella-zoster virus"; J. Med. Virol., vol. 70, pp. S71-S78; accepted Sep. 13, 2002, published 2003 (8 pages).
Sadzot-Delvaux, C. et al.; "An In Vivo Model of Varicella-Zoster Virus Latent Infection of Dorsal Root Ganglia"; J. Neurosci. Res., vol. 26, pp. 83-89; 1990 (7 pages).
Gershon, A. et al.; "Clinical Reinfection with Varicella-Zoster Virus"; Institute of Allergy and Infectious Diseases Collaborative Varicella Vaccine Study Group; Journal of Infectious Diseases, vol. 149, No. 2, pp. 137-142; Feb. 1984; retrieved from http://ww.jstor.org/stable/30109699 (7 pages).
Guess, H. A. et al.; "Epidemiology of Herpes Zoster in Children and Adolescents: A Population Based Study"; Pediatrics, vol. 76, No. 4, pp. 512-517; Oct. 1, 1985 (1 page).
Bogger-Goren, S. et al.; "Mucosal cell-mediated immunity to varicella-zoster virus: Role in protection against disease"; J. Pediatr. vol. 105, pp. 195-199; 1984 (5 pages).
Zaia, J. A. et al.; "Evaluation of Varicella-Zoster Immune Globulin: Protection of Immunosuppressed Children after Household Exposure to Varicella": J. Infect. Dis., vol. 147, No. 4, pp. 737-743; Apr. 1983 (7 pages).
Gershon, A.A. et al., NIAID-Collaborative-Varicella-Vaccine-Study-Group; "Live attenuated varicella vaccine: Efficacy for children with leukemia in remission"; JAMA, vol. 252, No. 3, pp. 355-362; Jul. 20, 1984 (8 pages).
Oxman, M.N. et al.; "A Vaccine to Prevent Herpes Zoster and Postherpetic Neuralgia in Older Adults"; N. Engl. J. Med., vol. 352, No. 22, pp. 2271-2284; Jun. 2, 2005 (14 pages).
Cunningham, A.L. et al.; "Efficacy of the Herpes Zoster Subunit Vaccine in Adults 70 Years of Age or Older"; N. Engl. J. Med., vol. 375, No. 11, pp. 1019-1032; Sep. 15, 2016 (14 pages).
Yi Xing et al.; "A site of varicella-zoster virus vulnerability identified by structural studies of neutralizing antibodies bound to the glycoprotein complex gHgL"; PNAS, vol. 112, No. 19, pp. 6056-6061; May 12, 2015; retrieved from www.pnas.org/cgi/doi/10.1073/pnas.1501176112 (15 pages).
Tang, Haikuan et al.; "Advances in the study of alpha herpesvirus gH and gL proteins"; Chinese Journal of Preventive Veterinary Medicine, vol. 29, No. 10, pp. 817-820; in Chinese with English translation; Oct. 2007 (10 pages).

* cited by examiner

SEQUENCE LISTING

```
<160> NUMBER OF SEQ ID NOS: 55

<210> SEQ ID NO 1
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 1

Gln Val Gln Leu Lys Glu Ser Gly Pro Gly Pro Val Lys Pro Ser Gln
1               5                   10                  15
```

Ser Leu Ser Leu Thr Cys Ser Val Thr Gly Tyr Ser Ile Thr Ser Gly
20 25 30

Asn Tyr Trp Asn Trp Val Arg Gln Phe Pro Gly Asn Lys Leu Glu Trp
35 40 45

Met Ala Tyr Ile Ser Tyr Asp Gly Ser Thr Tyr Tyr Asn Pro Ser Leu
50 55 60

Lys Asn Arg Ile Ser Ile Thr Arg Asp Thr Ser Lys Asn Gln Phe Phe
65 70 75 80

Leu Lys Leu Asn Ser Val Thr Thr Glu Asp Thr Ala Thr Tyr Tyr Cys
85 90 95

Ala Glu Gly Tyr Tyr Gly Tyr Trp Phe Ala Tyr Trp Gly Gln Gly Thr
100 105 110

Leu Val Thr Val Ser Ala
115

<210> SEQ ID NO 2
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 2

Glu Asn Val Leu Thr Gln Ser Pro Ala Ile Leu Ser Ala Ser Pro Gly
1 5 10 15

Glu Lys Val Thr Met Thr Cys Arg Ala Ser Ser Ser Val Ser Tyr Met
20 25 30

His Trp Tyr Gln Gln Lys Pro Gly Ser Ser Pro Lys Pro Trp Ile Tyr
35 40 45

Ala Thr Ser Asn Leu Ala Ser Gly Val Pro Ala Arg Phe Ser Gly Ser
50 55 60

Gly Ser Gly Thr Ser Tyr Ser Leu Thr Ile Ser Arg Val Glu Ala Glu
65 70 75 80

Asp Ala Ala Thr Tyr Tyr Cys Gln Gln Trp Ser Ser Asn Pro Phe Thr
85 90 95

Phe Gly Ser Gly Thr Lys Leu Glu Ile Lys
100 105

<210> SEQ ID NO 3
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 3

Glu Val Lys Leu Val Glu Ser Gly Pro Gly Leu Val Lys Pro Ser Gln
1 5 10 15

Ser Leu Ser Leu Thr Cys Ser Val Thr Gly Tyr Ser Ile Thr Ser Gly
20 25 30

Tyr Tyr Trp Asn Trp Ile Arg Gln Phe Pro Gly Asn Lys Leu Glu Trp
35 40 45

Met Gly Tyr Ile Ser Tyr Asp Gly Ser Asn Asn Tyr Asn Thr Ser Leu
50 55 60

Lys Asn Arg Ile Ser Ile Thr Arg Asp Thr Ser Lys Asn Gln Phe Phe
65 70 75 80

Leu Lys Leu Asn Ser Val Thr Thr Glu Asp Thr Ala Thr Tyr Tyr Cys

```
                85                  90                  95

Ala Arg Glu Asp Val Asn Tyr Pro Pro Tyr Ala Leu Asp Tyr Trp Gly
            100                 105                 110

Gln Gly Thr Ser Val Thr Val Ser Ser
        115                 120


<210> SEQ ID NO 4
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 4

Ser Ile Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Met Lys
            100                 105                 110


<210> SEQ ID NO 5
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 5

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Phe Ile Ser Asn Gly Gly Asp Asn Asn Tyr Tyr Ala Asp Thr Val
    50                  55                  60

Lys Gly Arg Phe Ile Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Asn Gly Asn Trp Gly Phe Ala Tyr Trp Gly Gln Gly Thr
            100                 105                 110

Leu Val Thr Val Ser Ala
        115


<210> SEQ ID NO 6
<211> LENGTH: 108
<212> TYPE: PRT
<213> ORGANISM: Artificial Sequence
<220> FEATURE:
```

<223> OTHER INFORMATION: Synthetic Polypeptide

<400> SEQUENCE: 6

```
Gln Asn Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Leu Thr Phe Gly Ala Gly Thr Lys Leu Glu Ile Lys
            100                 105
```

<210> SEQ ID NO 7
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 7

```
Glu Val Gln Leu Val Glu Ser Gly Gly Gly Val Val Gln Pro Gly Arg
1               5                   10                  15

Ser Leu Arg Leu Ser Cys Gly Ala Ser Gly Phe Thr Phe Asn Thr Tyr
            20                  25                  30

Ala Met His Trp Val Arg Gln Ala Pro Gly Lys Gly Met Glu Trp Val
        35                  40                  45

Ala Val Ile Ser Tyr Gly Gly Gly Asn Arg Tyr Tyr Ala Ala Ser Val
    50                  55                  60

Lys Gly Arg Phe Thr Ile Ser Arg Asp Asn Ser Lys Asn Thr Leu Phe
65                  70                  75                  80

Leu Gln Leu Asn Thr Leu Arg Pro Glu Asp Thr Ala Val Tyr Tyr Cys
                85                  90                  95

Ala Arg Ala Arg Asp Asn His Tyr Phe Phe Gly Met Asp Val Trp Gly
            100                 105                 110

Arg Gly Thr Thr Val Thr Val Ser Ser
        115                 120
```

<210> SEQ ID NO 8
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 8

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Glu Gly Phe Tyr Phe Pro Ile
                85                  90                  95

Asn Phe Gly Gly Gly Thr Lys Val Glu Ile Lys
            100                 105


<210> SEQ ID NO 9
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 9

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Thr Tyr Phe Pro Ile
                85                  90                  95

Asn Phe Gly Gly Gly Thr Lys Val Glu Ile Lys
            100                 105


<210> SEQ ID NO 10
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 10

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Tyr Phe Pro Ile
                85                  90                  95

Ala Phe Gly Gly Gly Thr Lys Val Glu Ile Lys
            100                 105


<210> SEQ ID NO 11
<211> LENGTH: 778
<212> TYPE: PRT
<213> ORGANISM: Varicella zoster
```

<400> SEQUENCE: 11

```
Asn Lys Ser Tyr Val Thr Pro Thr Pro Ala Thr Arg Ser Ile Gly His
1               5                   10                  15

Met Ser Ala Leu Leu Arg Glu Tyr Ser Asp Arg Asn Met Ser Leu Lys
            20                  25                  30

Leu Glu Ala Phe Tyr Pro Thr Gly Phe Asp Glu Glu Leu Ile Lys Ser
        35                  40                  45

Leu His Trp Gly Asn Asp Arg Lys His Val Phe Leu Val Ile Val Lys
    50                  55                  60

Val Asn Pro Thr Thr His Glu Gly Asp Val Gly Leu Val Ile Phe Pro
65                  70                  75                  80

Lys Tyr Leu Leu Ser Pro Tyr His Phe Lys Ala Glu His Arg Ala Pro
                85                  90                  95

Phe Pro Ala Gly Arg Phe Gly Phe Leu Ser His Pro Val Thr Pro Asp
            100                 105                 110

Val Ser Phe Phe Asp Ser Ser Phe Ala Pro Tyr Leu Thr Thr Gln His
        115                 120                 125

Leu Val Ala Phe Thr Thr Phe Pro Pro Asn Pro Leu Val Trp His Leu
    130                 135                 140

Glu Arg Ala Glu Thr Ala Ala Thr Ala Glu Arg Pro Phe Gly Val Ser
145                 150                 155                 160

Leu Leu Pro Ala Arg Pro Thr Val Pro Lys Asn Thr Ile Leu Glu His
                165                 170                 175

Lys Ala His Phe Ala Thr Trp Asp Ala Leu Ala Arg His Thr Phe Phe
            180                 185                 190

Ser Ala Glu Ala Ile Ile Thr Asn Ser Thr Leu Arg Ile His Val Pro
        195                 200                 205

Leu Phe Gly Ser Val Trp Pro Ile Arg Tyr Trp Ala Thr Gly Ser Val
    210                 215                 220

Leu Leu Thr Ser Asp Ser Gly Arg Val Glu Val Asn Ile Gly Val Gly
225                 230                 235                 240

Phe Met Ser Ser Leu Ile Ser Leu Ser Ser Gly Leu Pro Ile Glu Leu
                245                 250                 255

Ile Val Val Pro His Thr Val Lys Leu Asn Ala Val Thr Ser Asp Thr
            260                 265                 270

Thr Trp Phe Gln Leu Asn Pro Pro Gly Pro Asp Pro Gly Pro Ser Tyr
        275                 280                 285

Arg Val Tyr Leu Leu Gly Arg Gly Leu Asp Met Asn Phe Ser Lys His
    290                 295                 300

Ala Thr Val Asp Ile Cys Ala Tyr Pro Glu Glu Ser Leu Asp Tyr Arg
305                 310                 315                 320

Tyr His Leu Ser Met Ala His Thr Glu Ala Leu Arg Met Thr Thr Lys
                325                 330                 335

Ala Asp Gln His Asp Ile Asn Glu Glu Ser Tyr Tyr His Ile Ala Ala
            340                 345                 350

Arg Ile Ala Thr Ser Ile Phe Ala Leu Ser Glu Met Gly Arg Thr Thr
        355                 360                 365

Glu Tyr Phe Leu Leu Asp Glu Ile Val Asp Val Gln Tyr Gln Leu Lys
    370                 375                 380

Phe Leu Asn Tyr Ile Leu Met Arg Ile Gly Ala Gly Ala His Pro Asn
385                 390                 395                 400

Thr Ile Ser Gly Thr Ser Asp Leu Ile Phe Ala Asp Pro Ser Gln Leu
                405                 410                 415
```

His Asp Glu Leu Ser Leu Leu Phe Gly Gln Val Lys Pro Ala Asn Val
420 425 430

Asp Tyr Phe Ile Ser Tyr Asp Glu Ala Arg Asp Gln Leu Lys Thr Ala
435 440 445

Tyr Ala Leu Ser Arg Gly Gln Asp His Val Asn Ala Leu Ser Leu Ala
450 455 460

Arg Arg Val Ile Met Ser Ile Tyr Lys Gly Leu Leu Val Lys Gln Asn
465 470 475 480

Leu Asn Ala Thr Glu Arg Gln Ala Leu Phe Phe Ala Ser Met Ile Leu
485 490 495

Leu Asn Phe Arg Glu Gly Leu Glu Asn Ser Ser Arg Val Leu Asp Gly
500 505 510

Arg Thr Thr Leu Leu Leu Met Thr Ser Met Cys Thr Ala Ala His Ala
515 520 525

Thr Gln Ala Ala Leu Asn Ile Gln Glu Gly Leu Ala Tyr Leu Asn Pro
530 535 540

Ser Lys His Met Phe Thr Ile Pro Asn Val Tyr Ser Pro Cys Met Gly
545 550 555 560

Ser Leu Arg Thr Asp Leu Thr Glu Glu Ile His Val Met Asn Leu Leu
565 570 575

Ser Ala Ile Pro Thr Arg Pro Gly Leu Asn Glu Val Leu His Thr Gln
580 585 590

Leu Asp Glu Ser Glu Ile Phe Asp Ala Ala Phe Lys Thr Met Met Ile
595 600 605

Phe Thr Thr Trp Thr Ala Lys Asp Leu His Ile Leu His Thr His Val
610 615 620

Pro Glu Val Phe Thr Cys Gln Asp Ala Ala Ala Arg Asn Gly Glu Tyr
625 630 635 640

Val Leu Ile Leu Pro Ala Val Gln Gly His Ser Tyr Val Ile Thr Arg
645 650 655

Asn Lys Pro Gln Arg Gly Leu Val Tyr Ser Leu Ala Asp Val Asp Val
660 665 670

Tyr Asn Pro Ile Ser Val Val Tyr Leu Ser Lys Asp Thr Cys Val Ser
675 680 685

Glu His Gly Val Ile Glu Thr Val Ala Leu Pro His Pro Asp Asn Leu
690 695 700

Lys Glu Cys Leu Tyr Cys Gly Ser Val Phe Leu Arg Tyr Leu Thr Thr
705 710 715 720

Gly Ala Ile Met Asp Ile Ile Ile Ile Asp Ser Lys Asp Thr Glu Arg
725 730 735

Gln Leu Ala Ala Met Gly Asn Ser Thr Ile Pro Pro Phe Asn Pro Asp
740 745 750

Met His Gly Asp Asp Ser Lys Ala Val Leu Leu Phe Pro Asn Gly Thr
755 760 765

Val Val Thr Leu Leu Gly Phe Glu Arg Arg
770 775

<210> SEQ ID NO 12
<211> LENGTH: 138
<212> TYPE: PRT
<213> ORGANISM: Varicella zoster

<400> SEQUENCE: 12

Leu His Leu Gln Asp Asp Thr Pro Leu Phe Phe Gly Ala Lys Pro Leu

```
1               5                   10                  15

Ser Asp Val Ser Leu Ile Ile Thr Glu Pro Cys Val Ser Ser Val Tyr
            20                  25                  30

Glu Ala Trp Asp Tyr Ala Ala Pro Pro Val Ser Asn Leu Ser Glu Ala
        35                  40                  45

Leu Ser Gly Ile Val Val Lys Thr Lys Cys Pro Val Pro Glu Val Ile
    50                  55                  60

Leu Trp Phe Lys Asp Lys Gln Met Ala Tyr Trp Thr Asn Pro Tyr Val
65                  70                  75                  80

Thr Leu Lys Gly Leu Thr Gln Ser Val Gly Glu Glu His Lys Ser Gly
                85                  90                  95

Asp Ile Arg Asp Ala Leu Leu Asp Ala Leu Ser Gly Val Trp Val Asp
            100                 105                 110

Ser Thr Pro Ser Ser Thr Asn Ile Pro Glu Asn Gly Cys Val Trp Gly
        115                 120                 125

Ala Asp Arg Leu Phe Gln Arg Val Cys Gln
    130                 135


<210> SEQ ID NO 13
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 13

His His His His His His
1               5


<210> SEQ ID NO 14
<211> LENGTH: 330
<212> TYPE: PRT
<213> ORGANISM: Homo sapiens

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 15
<211> LENGTH: 326
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
```

```
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 16
<211> LENGTH: 327
<212> TYPE: PRT
<213> ORGANISM: Homo sapiens

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 17
<211> LENGTH: 324
<212> TYPE: PRT
<213> ORGANISM: Mus musculus

<400> SEQUENCE: 17

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Glu Ser Asp Leu Tyr Thr Leu
    50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asn Thr Asn Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300
```

Leu His Glu Gly Leu His Asn His His Thr Glu Lys Ser Leu Ser His
305 310 315 320

Ser Pro Gly Lys

<210> SEQ ID NO 18
<211> LENGTH: 330
<212> TYPE: PRT
<213> ORGANISM: Mus musculus

<400> SEQUENCE: 18

Ala Lys Thr Thr Ala Pro Ser Val Tyr Pro Leu Ala Pro Val Cys Gly
1 5 10 15

Asp Thr Thr Gly Ser Ser Val Thr Leu Gly Cys Leu Val Lys Gly Tyr
20 25 30

Phe Pro Glu Pro Val Thr Leu Thr Trp Asn Ser Gly Ser Leu Ser Ser
35 40 45

Gly Val His Thr Phe Pro Ala Val Leu Gln Ser Asp Leu Tyr Thr Leu
50 55 60

Ser Ser Ser Val Thr Val Thr Ser Ser Thr Trp Pro Ser Gln Ser Ile
65 70 75 80

Thr Cys Asn Val Ala His Pro Ala Ser Ser Thr Lys Val Asp Lys Lys
85 90 95

Ile Glu Pro Arg Gly Pro Thr Ile Lys Pro Cys Pro Pro Cys Lys Cys
100 105 110

Pro Ala Pro Asn Leu Leu Gly Gly Pro Ser Val Phe Ile Phe Pro Pro
115 120 125

Lys Ile Lys Asp Val Leu Met Ile Ser Leu Ser Pro Ile Val Thr Cys
130 135 140

Val Val Val Asp Val Ser Glu Asp Asp Pro Asp Val Gln Ile Ser Trp
145 150 155 160

Phe Val Asn Asn Val Glu Val His Thr Ala Gln Thr Gln Thr His Arg
165 170 175

Glu Asp Tyr Asn Ser Thr Leu Arg Val Val Ser Ala Leu Pro Ile Gln
180 185 190

His Gln Asp Trp Met Ser Gly Lys Glu Phe Lys Cys Lys Val Asn Asn
195 200 205

Lys Asp Leu Pro Ala Pro Ile Glu Arg Thr Ile Ser Lys Pro Lys Gly
210 215 220

Ser Val Arg Ala Pro Gln Val Tyr Val Leu Pro Pro Pro Glu Glu Glu
225 230 235 240

Met Thr Lys Lys Gln Val Thr Leu Thr Cys Met Val Thr Asp Phe Met
245 250 255

Pro Glu Asp Ile Tyr Val Glu Trp Thr Asn Asn Gly Lys Thr Glu Leu
260 265 270

Asn Tyr Lys Asn Thr Glu Pro Val Leu Asp Ser Asp Gly Ser Tyr Phe
275 280 285

Met Tyr Ser Lys Leu Arg Val Glu Lys Lys Asn Trp Val Glu Arg Asn
290 295 300

Ser Tyr Ser Cys Ser Val Val His Glu Gly Leu His Asn His His Thr
305 310 315 320

Thr Lys Ser Phe Ser Arg Thr Pro Gly Lys
325 330

<210> SEQ ID NO 19

-continued

<211> LENGTH: 107
<212> TYPE: PRT
<213> ORGANISM: Homo sapiens

<400> SEQUENCE: 19

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 20
<211> LENGTH: 106
<212> TYPE: PRT
<213> ORGANISM: Homo sapiens

<400> SEQUENCE: 20

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 21
<211> LENGTH: 107
<212> TYPE: PRT
<213> ORGANISM: Mus musculus

<400> SEQUENCE: 21

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

```
Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105


<210> SEQ ID NO 22
<211> LENGTH: 106
<212> TYPE: PRT
<213> ORGANISM: Mus musculus

<400> SEQUENCE: 22

Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
            20                  25                  30

Phe Tyr Pro Gly Val Val Thr Val Asp Trp Lys Val Asp Gly Thr Pro
        35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
                85                  90                  95

Glu Lys Ser Leu Ser Arg Ala Asp Cys Ser
            100                 105


<210> SEQ ID NO 23
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 23

tgcatttgaa ctccttgcc                                                  19


<210> SEQ ID NO 24
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 24

ccatcaatct tccacttgac                                                 20


<210> SEQ ID NO 25
<211> LENGTH: 239
<212> TYPE: PRT
<213> ORGANISM: Artificial Sequence
<220> FEATURE:
<223> OTHER INFORMATION: Synthetic Polypeptide

<400> SEQUENCE: 25

Gln Val Gln Leu Lys Glu Ser Gly Pro Gly Pro Val Lys Pro Ser Gln
1               5                   10                  15

Ser Leu Ser Leu Thr Cys Ser Val Thr Gly Tyr Ser Ile Thr Ser Gly
            20                  25                  30

Asn Tyr Trp Asn Trp Val Arg Gln Phe Pro Gly Asn Lys Leu Glu Trp
        35                  40                  45

Met Ala Tyr Ile Ser Tyr Asp Gly Ser Thr Tyr Tyr Asn Pro Ser Leu
```

50 55 60

Lys Asn Arg Ile Ser Ile Thr Arg Asp Thr Ser Lys Asn Gln Phe Phe
65 70 75 80

Leu Lys Leu Asn Ser Val Thr Thr Glu Asp Thr Ala Thr Tyr Tyr Cys
85 90 95

Ala Glu Gly Tyr Tyr Gly Tyr Trp Phe Ala Tyr Trp Gly Gln Gly Thr
100 105 110

Leu Val Thr Val Ser Ala Gly Gly Gly Gly Ser Gly Gly Gly Gly Ser
115 120 125

Gly Gly Gly Gly Ser Glu Asn Val Leu Thr Gln Ser Pro Ala Ile Leu
130 135 140

Ser Ala Ser Pro Gly Glu Lys Val Thr Met Thr Cys Arg Ala Ser Ser
145 150 155 160

Ser Val Ser Tyr Met His Trp Tyr Gln Gln Lys Pro Gly Ser Ser Pro
165 170 175

Lys Pro Trp Ile Tyr Ala Thr Ser Asn Leu Ala Ser Gly Val Pro Ala
180 185 190

Arg Phe Ser Gly Ser Gly Ser Gly Thr Ser Tyr Ser Leu Thr Ile Ser
195 200 205

Arg Val Glu Ala Glu Asp Ala Ala Thr Tyr Tyr Cys Gln Gln Trp Ser
210 215 220

Ser Asn Pro Phe Thr Phe Gly Ser Gly Thr Lys Leu Glu Ile Lys
225 230 235

<210> SEQ ID NO 26
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 26

Glu Val Lys Leu Val Glu Ser Gly Pro Gly Leu Val Lys Pro Ser Gln
1 5 10 15

Ser Leu Ser Leu Thr Cys Ser Val Thr Gly Tyr Ser Ile Thr Ser Gly
20 25 30

Tyr Tyr Trp Asn Trp Ile Arg Gln Phe Pro Gly Asn Lys Leu Glu Trp
35 40 45

Met Gly Tyr Ile Ser Tyr Asp Gly Ser Asn Asn Tyr Asn Thr Ser Leu
50 55 60

Lys Asn Arg Ile Ser Ile Thr Arg Asp Thr Ser Lys Asn Gln Phe Phe
65 70 75 80

Leu Lys Leu Asn Ser Val Thr Thr Glu Asp Thr Ala Thr Tyr Tyr Cys
85 90 95

Ala Arg Glu Asp Val Asn Tyr Pro Pro Tyr Ala Leu Asp Tyr Trp Gly
100 105 110

Gln Gly Thr Ser Val Thr Val Ser Ser Gly Gly Gly Gly Ser Gly Gly
115 120 125

Gly Gly Ser Gly Gly Gly Gly Ser Ser Ile Val Met Thr Gln Thr Pro
130 135 140

Leu Ser Leu Pro Val Ser Leu Gly Asp Gln Ala Ser Ile Ser Cys Arg
145 150 155 160

Ser Ser Gln Ser Leu Val His Ser Asn Gly Asn Thr Tyr Leu His Trp
165 170 175

Tyr Leu Gln Lys Pro Gly Gln Ser Pro Lys Leu Leu Ile Tyr Lys Val

```
            180                 185                 190

Ser Asn Arg Phe Ser Gly Val Pro Asp Arg Phe Ser Gly Ser Gly Ser
        195                 200                 205

Gly Thr Asp Phe Thr Leu Lys Ile Ser Arg Val Glu Ala Glu Asp Leu
    210                 215                 220

Gly Val Tyr Phe Cys Ser Gln Ser Thr His Val Pro Trp Thr Phe Gly
225                 230                 235                 240

Gly Gly Thr Lys Leu Glu Met Lys
                245


<210> SEQ ID NO 27
<211> LENGTH: 241
<212> TYPE: PRT
<213> ORGANISM: Artificial Sequence
<220> FEATURE:
<223> OTHER INFORMATION: Synthetic Polypeptide

<400> SEQUENCE: 27

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Phe Ile Ser Asn Gly Gly Asp Asn Asn Tyr Tyr Ala Asp Thr Val
    50                  55                  60

Lys Gly Arg Phe Ile Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Asn Gly Asn Trp Gly Phe Ala Tyr Trp Gly Gln Gly Thr
            100                 105                 110

Leu Val Thr Val Ser Ala Gly Gly Gly Gly Ser Gly Gly Gly Gly Ser
        115                 120                 125

Gly Gly Gly Gly Ser Gln Asn Val Leu Thr Gln Ser Pro Thr Thr Met
    130                 135                 140

Ala Ala Ser Pro Gly Glu Lys Ile Thr Ile Thr Cys Ser Ala Ser Ser
145                 150                 155                 160

Ser Ile Ser Ser Asn Tyr Leu His Trp Tyr Gln Gln Lys Pro Gly Phe
                165                 170                 175

Ser Pro Lys Leu Leu Ile Tyr Arg Thr Ser Asn Leu Ala Ser Gly Val
            180                 185                 190

Pro Ala Arg Phe Ser Gly Ser Gly Ser Gly Thr Ser Tyr Ser Leu Thr
        195                 200                 205

Ile Gly Thr Met Glu Ala Glu Asp Val Ala Thr Tyr Tyr Cys Gln Gln
    210                 215                 220

Gly Ser Ser Ile Pro Leu Thr Phe Gly Ala Gly Thr Lys Leu Glu Ile
225                 230                 235                 240

Lys


<210> SEQ ID NO 28
<211> LENGTH: 107
<212> TYPE: PRT
<213> ORGANISM: Artificial Sequence
<220> FEATURE:
<223> OTHER INFORMATION: Synthetic Polypeptide
```

<400> SEQUENCE: 28

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asn Ser Phe Pro Leu
85 90 95

Thr Phe Gly Gly Gly Thr Lys Val Glu Ile Lys
100 105

<210> SEQ ID NO 29
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 29

Ser Gly Asn Tyr Trp Asn
1 5

<210> SEQ ID NO 30
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 30

Tyr Ile Ser Tyr Asp Gly Ser Thr Tyr Tyr Asn Pro Ser Leu Lys Asn
1 5 10 15

<210> SEQ ID NO 31
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 31

Gly Tyr Tyr Gly Tyr Trp Phe Ala Tyr
1 5

<210> SEQ ID NO 32
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 32

Arg Ala Ser Ser Ser Val Ser Tyr Met His
1 5 10

<210> SEQ ID NO 33
<211> LENGTH: 7
<212> TYPE: PRT

<213> ORGANISM: Artificial Sequence
<220> FEATURE:
<223> OTHER INFORMATION: Synthetic Polypeptide

<400> SEQUENCE: 33

Ala Thr Ser Asn Leu Ala Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 34

Gln Gln Trp Ser Ser Asn Pro Phe Thr
1               5

<210> SEQ ID NO 35
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 35

Glu Asp Val Asn Tyr Pro Pro Tyr Ala Leu Asp Tyr
1               5                   10

<210> SEQ ID NO 36
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 36

Arg Ser Ser Gln Ser Leu Val His Ser Asn Gly Asn Thr Tyr Leu His
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 37

Lys Val Ser Asn Arg Phe Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 38

Ser Gln Ser Thr His Val Pro Trp Thr
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 39

Ser Tyr Thr Met Ser
1 5

<210> SEQ ID NO 40
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 40

Phe Ile Ser Asn Gly Gly Asp Asn Asn Tyr Tyr Ala Asp Thr Val Lys
1 5 10 15

Gly

<210> SEQ ID NO 41
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 41

His Asn Gly Asn Trp Gly Phe Ala Tyr
1 5

<210> SEQ ID NO 42
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 42

Ser Ala Ser Ser Ser Ile Ser Ser Asn Tyr Leu His
1 5 10

<210> SEQ ID NO 43
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 43

Arg Thr Ser Asn Leu Ala Ser
1 5

<210> SEQ ID NO 44
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 44

Gln Gln Gly Ser Ser Ile Pro Leu Thr
1 5

<210> SEQ ID NO 45
<211> LENGTH: 5
<212> TYPE: PRT

```
<213> ORGANISM: Artificial Sequence
<220> FEATURE:
<223> OTHER INFORMATION: Synthetic Polypeptide

<400> SEQUENCE: 45

Thr Tyr Ala Met His
1               5


<210> SEQ ID NO 46
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 46

Val Ile Ser Tyr Gly Gly Gly Asn Arg Tyr Tyr Ala Ala Ser Val Lys
1               5                   10                  15

Gly


<210> SEQ ID NO 47
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 47

Ala Arg Asp Asn His Tyr Phe Phe Gly Met Asp Val
1               5                   10


<210> SEQ ID NO 48
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 48

Arg Ala Ser Gln Gly Ile Ser Ser Trp Leu Ala
1               5                   10


<210> SEQ ID NO 49
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 49

Ala Ala Ser Ser Leu Gln Ser
1               5


<210> SEQ ID NO 50
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 50

Gln Gln Ala Asn Ser Phe Pro Leu Thr
1               5


<210> SEQ ID NO 51
<211> LENGTH: 9
```

-continued

```
<212> TYPE: PRT
<213> ORGANISM: Artificial Sequence
<220> FEATURE:
<223> OTHER INFORMATION: Synthetic Polypeptide

<400> SEQUENCE: 51

Gln Glu Gly Phe Tyr Phe Pro Ile Asn
1               5


<210> SEQ ID NO 52
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 52

Gln Gln Ala Thr Tyr Phe Pro Ile Asn
1               5


<210> SEQ ID NO 53
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 53

Gln Gln Ser Ser Tyr Phe Pro Ile Ala
1               5


<210> SEQ ID NO 54
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 54

Ser Gly Tyr Tyr Trp Asn
1               5


<210> SEQ ID NO 55
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 55

Tyr Ile Ser Tyr Asp Gly Ser Asn Asn Tyr Asn Thr Ser Leu Lys Asn
1               5                   10                  15
```

ANTI-VARICELLA-ZOSTER VIRUS ANTIBODY AND USE THEREOF

CROSS REFERENCE TO RELATED APPLICATION

This application is a 35 U.S.C. § 371 National Phase Application of International Application No. PCT/CN2022/073199, filed Jan. 21, 2022, which designates the U.S. and claims the benefit of priority under 35 U.S.C. § 119(a) of Chinese Patent Application No. 202110259834.4, filed on Mar. 10, 2021, each of which is hereby incorporated by reference herein in its entirety.

SEQUENCE LISTING

The instant application contains a Sequence Listing which has been submitted electronically in ASCII format and is hereby incorporated by reference in its entirety. Said ASCII copy, created on Oct. 10, 2023, is named 078291-000310USPX2_SL.txt and is 51,020 bytes in size.

TECHNICAL FIELD

The present application generally relates to the field of genetic engineering and antibody medicine. In particular, the present application relates to an anti-varicella-zoster virus antibody and use thereof. Developed in the present application is a novel anti-varicella-zoster virus antibody, and provided in the present application is a use of the antibody in the prevention or treatment of varicella and zoster.

BACKGROUND

Varicella-zoster virus (VZV) belongs to the genus Herpesvirus, alpha subfamily Herpesvirus, and is an enveloped DNA virus. VZV is the smallest human herpes virus, having a genome length of approximately 125,000 bp, including more than 70 open reading frames, and encoding a variety of proteins (Davison, A. J., and J. E. Scott. 1986). There are at least six surface glycoproteins in VZV, such as gB (gp II), gC (gp IV), gE (gp I), gH (gp III), gI and gL. Glycoproteins gE, gB and gH are extremely abundant on the cell membranes of infected cells, and the antibodies induced by them are capable of neutralizing viruses (Davison, A. J., C. M. Edson. 1986). Glycoprotein gE is expressed in highest abundance in VZV-infected cells, is non-covalently linked to gI protein, and binds to the Fc segment of immunoglobulin IgG. The gB protein is the target of neutralizing antibodies and plays a role in viral invasion of the host cells. The amino acid sequence of gB protein is highly conserved in VZV and herpes simplex virus-1 (HSV-1) (Kapsenberk, J. G. 1964). The gH protein mediates the fusion between the viral envelope and the cell membrane as well as between cell membranes, facilitating virus spread among cells. Only coexpression of the gH protein with the gL protein allows the gH protein to be glycosylated and translocated to the cell surface (Forghani, B., L. Ni, and C. Grose. 1994).

VZV can infect human diploid cells and melanoma cells and can also replicate in VERO cells and primary African green monkey kidney cells. VZV enters cells by adsorbing heparin sulfate proteoglycans on the cell surface and then binding to a low-affinity second receptor, expresses viral proteins within the infected cells to make the cells form multinucleated giant cells (Zhu, Z., M. D. Gershon. 1995). Most viral particles are remained in the cytoplasmic vacuoles. Few free viruses are released to the outside of the cells.

VZV has only one serotype. Its genetic diversity is limited, and this genetic diversity does not affect its infectivity and virulence. VZV infection is highly species-specific. VAV has no animal reservoir hosts. Although it can infect some non-human primates and small animals, such as guinea pigs (Chen, J. 2003) and rats (Sadzot-Delvaux. 1990), it does not cause diseases in these animals. Human is the only known natural host, and the skin is the main target organ of the virus. VZV can be transmitted via droplets and/or contact. First infection in children mainly causes varicella. Varicella is prevalent in temperate areas, and usually occurs in winter and spring. Lifelong immunity is generated after varicella infection, and cases of second infection are rare (Gershon, A. A. 1984). Residual VZV in the infected individuals can retrograde along the sensory nerve axons, or can be transferred to spinal dorsal root ganglia or cranial ganglia after fusing with neuron cells via infected T cells and lurks in the ganglia. When the body's immunity is lowered, the latent viruses are activated and replicated in large numbers, transferred to the skin through the sensory nerve axons, and causes herpes zoster as VZV-specific cellular immunity decreases. As herpes zoster arises from the reactivation of the latent viruses, so only patients with primary infection will suffer from herpes zoster, and the onset is not seasonal. Herpes zoster occurs mainly in people over 45 years old, and the incidence rate increases with age. The incidence rate of herpes zoster in the general population is (3-5)/1000 persons/year, with an annual increase of 2.5-5.0%. The incidence rate of herpes zoster in people over 75 years old can reach 10/1000 persons/year, and the incidence rate of herpes zoster in children is very low (Guess, H. A. 1985). Herpes zoster is more common in patients receiving immunosuppressive therapy and in patients with HIV infection. Herpes zoster is accompanied by severe pain in addition to skin lesions, and a common complication is Post Herpetic Neuralgia (PHN), which can last for months to years.

IgG, IgM and IgA antibodies are produced as a result of VZV infection. These antibodies bind to viral proteins including glycoproteins, regulatory proteins, structural proteins and enzymes (Bogger-Goren. 1984). The neutralizing antibodies mediate lysis of infected cells. Neutralizing antibodies that bind to the gE and gI proteins require complements for their neutralizing action, whereas antibodies that bind to the gB and gH/gL proteins do not require complements. IgG antibodies, especially antibodies against glycoproteins, exist in the body for a long time after first infection with varicella, protecting the body from second infection. Injection of immunoglobulins against VZV within 72 hours after exposure to VZV in neonates, unimmunized pregnant women, or immunocompromised individuals can inhibit infection and viral replication in the body (Zaia, J. A., 1983), reduce the severity of varicella and decrease the risk of varicella pneumonia, but injection of immunoglobulins in children with acute varicella cannot clinically ameliorate the course of the disease. Antiviral drugs can effectively reduce the severity of varicella and herpes zoster, shorten the disease course, and reduce the incidence of postherpetic neuralgia. At present, the treatment of herpes zoster is mainly non-specific antiviral therapy, with no specific antiviral drug.

Therefore, it is of great biological and medical significance to explore and develop anti-varicella-zoster virus antibodies due to clinical needs.

SUMMARY OF THE INVENTION

In a first aspect, there is provided in the present application an antibody against varicella-zoster virus comprising a heavy chain variable region comprising the amino acid sequences of HCDR1, HCDR2 and HCDR3 and a light chain variable region comprising the amino acid sequences of LCDR1, LCDR2 and LCDR3, wherein the amino acid sequence of HCDR1 is SGNYWN (SEQ ID NO: 29), the amino acid sequence of HCDR2 is YISYDG-STYYNPSLKN (SEQ ID NO: 30), the amino acid sequence of HCDR3 is GYYGYWFAY (SEQ ID NO: 31), the amino acid sequence of LCDR1 is RASSSVSYMH (SEQ ID NO: 32), the amino acid sequence of LCDR2 is ATSNLAS (SEQ ID NO: 33), and the amino acid sequence of LCDR3 is QQWSSNPFT (SEQ ID NO: 34); or the amino acid sequence of HCDR1 is SGYYWN (SEQ ID NO: 54), the amino acid sequence of HCDR2 is YISYDGSNNYNT-SLKN (SEQ ID NO: 55), the amino acid sequence of HCDR3 is EDVNYPPYALDY (SEQ ID NO: 35), the amino acid sequence of LCDR1 is RSSQSLVHSNGNTYLH (SEQ ID NO: 36), the amino acid sequence of LCDR2 is KVSNRFS (SEQ ID NO: 37), and the amino acid sequence of LCDR3 is SQSTHVPWT (SEQ ID NO: 38); or the amino acid sequence of HCDR1 is SYTMS (SEQ ID NO: 39), the amino acid sequence of HCDR2 is FISNGGDNNYY-ADTVKG (SEQ ID NO: 40), the amino acid sequence of HCDR3 is HNGNWGFAY (SEQ ID NO: 41), the amino acid sequence of LCDR1 is SASSSISSNYLH (SEQ ID NO: 42), the amino acid sequence of LCDR2 is RTSNLAS (SEQ ID NO: 43), and the amino acid sequence of LCDR3 is QQGSSIPLT (SEQ ID NO: 44); or the amino acid sequence of HCDR1 is TYAMH (SEQ ID NO: 45), the amino acid sequence of HCDR2 is VISYGGGNRYYAASVKG (SEQ ID NO: 46), the amino acid sequence of HCDR3 is ARDN-HYFFGMDV (SEQ ID NO: 47), the amino acid sequence of LCDR1 is RASQGISSWLA (SEQ ID NO: 48), the amino acid sequence of LCDR2 is AASSLQS (SEQ ID NO: 49), and the amino acid sequence of LCDR3 is QQANSFPLT (SEQ ID NO: 50), QEGFYFPIN (SEQ ID NO: 51), QQATYFPIN (SEQ ID NO: 52) or QQSSYFPIA (SEQ ID NO: 53); wherein the amino acid sequences of HCDRs and LCDRs are defined according to Kabat.

In some embodiments of the first aspect, the amino acid sequence of the heavy chain variable region of the antibody is set forth in SEQ ID NO: 1, 3, 5, or 7.

In some embodiments of the first aspect, the amino acid sequence of the light chain variable region of the antibody is set forth in SEQ ID NO: 2, 4, 6, 8, 9, 10, or 28.

In some embodiments of the first aspect, the amino acid sequence of the heavy chain variable region of the antibody is set forth in SEQ ID NO:1, and the amino acid sequence of the light chain variable region of the antibody is set forth in SEQ ID NO:2; or the amino acid sequence of the heavy chain variable region of the antibody is set forth in SEQ ID NO:3, and the amino acid sequence of the light chain variable region of the antibody is set forth in SEQ ID NO:4; or the amino acid sequence of the heavy chain variable region of the antibody is set forth in SEQ ID NO:5, and the amino acid sequence of the light chain variable region of the antibody is set forth in SEQ ID NO:6; the amino acid sequence of the heavy chain variable region of the antibody is set forth in SEQ ID NO:7, and the amino acid sequence of the light chain variable region of the antibody is set forth in SEQ ID NO:8; or the amino acid sequence of the heavy chain variable region of the antibody is set forth in SEQ ID NO:7, and the amino acid sequence of the light chain variable region of the antibody is set forth in SEQ ID NO:9; or the amino acid sequence of the heavy chain variable region of the antibody is set forth in SEQ ID NO:7, and the amino acid sequence of the light chain variable region of the antibody is set forth in SEQ ID NO:10; or the amino acid sequence of the heavy chain variable region of the antibody is set forth in SEQ ID NO:7, and the amino acid sequence of the light chain variable region of the antibody is set forth in SEQ ID NO:28.

In a second aspect, there is provided in the present application an antibody against varicella-zoster virus, wherein the amino acid sequence of the heavy chain variable region of the antibody has at least 90% identity to the amino acid sequence as set forth in any one of SEQ ID NOs: 1, 3, 5, and 7, and the amino acid sequence of the light chain variable region of the antibody has at least 90% identity to the amino acid sequence as set forth in any one of SEQ ID NOs: 2, 4, 6, 8, 9, 10, and 28.

In some embodiments of the first and second aspects, the antibody is a whole antibody, a Fab fragment, a $F(ab')_2$ fragment, or a single chain Fv (scFv).

In some embodiments of the first and second aspects, the antibody is a monoclonal antibody.

In some embodiments of the first and second aspects, the antibody further comprises a heavy chain constant region selected from an IgG1 subtype, an IgG2 subtype, or an IgG4 subtype.

In some embodiments of the first aspect and the second aspect, the antibody further comprises a light chain constant region selected from a kappa subtype or a lamda subtype.

In some embodiments of the first and second aspects, the antibody binds to the gH/gL protein of varicella-zoster virus; and/or the antibody mediates antibody-dependent cell-mediated cytotoxicity (ADCC).

In a third aspect, there is provided in the present application a nucleic acid molecule encoding the antibody of the first or second aspect.

In a fourth aspect, there is provided in the present application a pharmaceutical composition comprising the antibody of the first or second aspect and a pharmaceutically acceptable excipient, diluent or carrier.

In a fifth aspect, there is provided in the present application use of the antibody of the first or second aspect, the nucleic acid molecule of the third aspect, or the pharmaceutical composition of the fourth aspect in the manufacture of a medicament for the prevention or treatment of varicella and herpes zoster.

In a sixth aspect, there is provided in the present application a method of preventing or treating varicella and herpes zoster, comprising administering to a subject in need thereof the antibody of the first or second aspect, or the pharmaceutical composition of the fourth aspect.

DESCRIPTION OF THE SEQUENCES

Figures 1A, 1B, 1C:
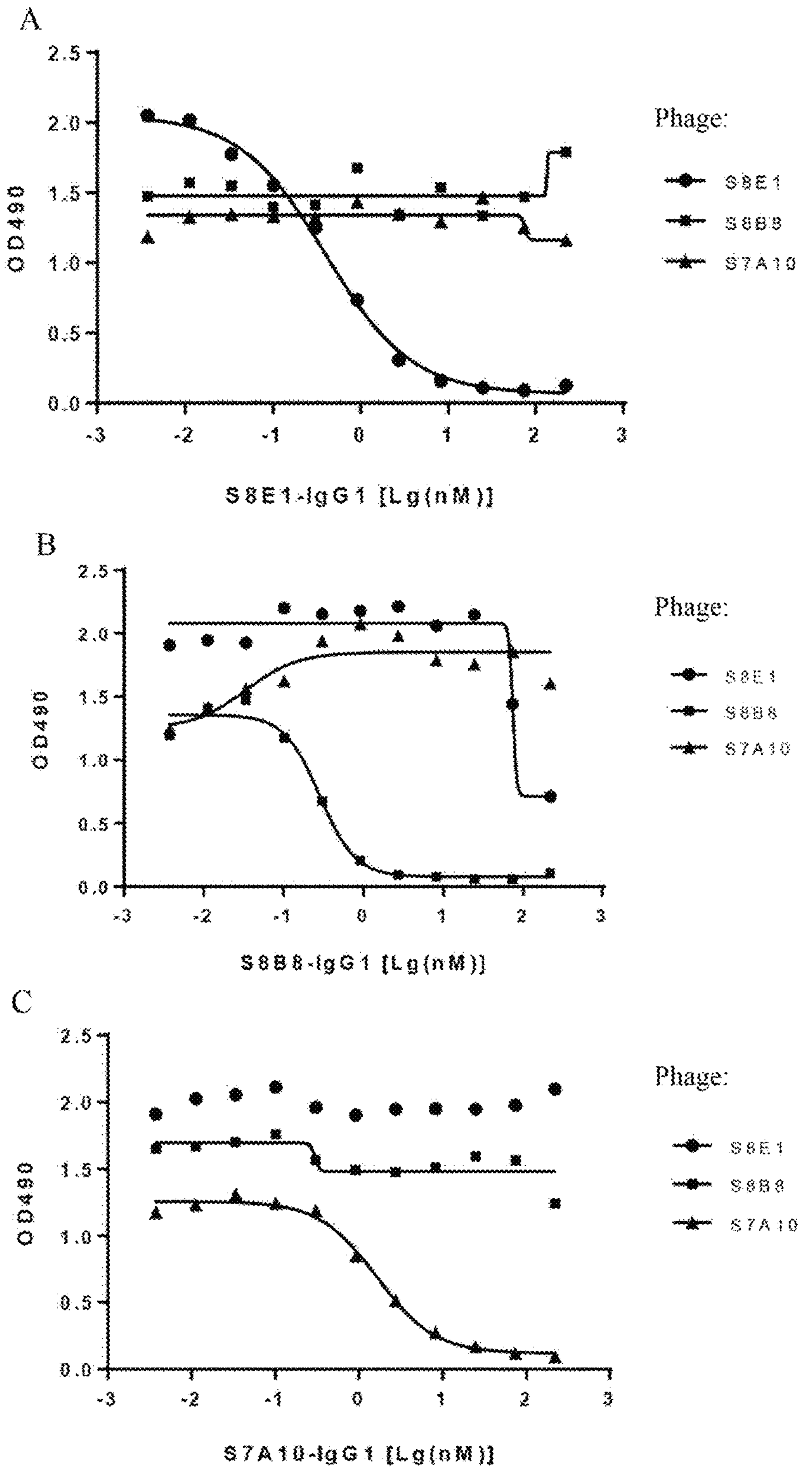
FIGS. 1A-IC show the results from an ELISA assay assessing the ability of the monoclonal antibodies against the varicella-zoster virus recombinant protein gH/gL to block the binding of purified anti-recombinant protein gH/gL phages to varicella-zoster virus recombinant protein gH/gL. Panels A-C show the blocking results of the monoclonal antibodies S8E1, S8B8 and S7A10against the varicella-zoster virus recombinant protein gH/gL, respectively.

SEQ ID NO:1 shows the amino acid sequence of the heavy chain variable region of the monoclonal antibody S7A10.

SEQ ID NO:2 shows the amino acid sequence of the light chain variable region of the monoclonal antibody S7A10.

SEQ ID NO:3 shows the amino acid sequence of the heavy chain variable region of the monoclonal antibody S8E1.

SEQ ID NO:4 shows the amino acid sequence of the light chain variable region of the monoclonal antibody S8E1.

SEQ ID NO:5 shows the amino acid sequence of the heavy chain variable region of the monoclonal antibody S8B8.

SEQ ID NO:6 shows the amino acid sequence of the light chain variable region of the monoclonal antibody S8B8.

SEQ ID NO:7 shows the amino acid sequence of the heavy chain variable regions of the monoclonal antibodies H4H8-L1B7, H4H8-L14H8, H4H8-L13C1 and H4H8-L13C7.

SEQ ID NO:8 shows the amino acid sequence of the light chain variable region of the monoclonal antibody H4H8-L13C1.

SEQ ID NO:9 shows the amino acid sequence of the light chain variable region of the monoclonal antibody H4H8-L13C7.

SEQ ID NO:10 shows the amino acid sequence of the light chain variable region of the monoclonal antibody H4H8-L14H8.

SEQ ID NO:11 shows the amino acid sequence of the gH glycoprotein of varicella-zoster virus.

SEQ ID NO:12 shows the amino acid sequence of the gL glycoprotein of varicella-zoster virus.

SEQ ID NO:13 shows the amino acid sequence of the His tag.

SEQ ID NO:14 shows the amino acid sequence of the heavy chain constant region of human (*Homo sapiens*) IgG1 subtype.

SEQ ID NO:15 shows the amino acid sequence of the heavy chain constant region of human (*Homo sapiens*) IgG2 subtype.

SEQ ID NO:16 shows the amino acid sequence of the heavy chain constant region of human (*Homo sapiens*) IgG4 subtype.

SEQ ID NO:17 shows the amino acid sequence of the heavy chain constant region of mouse (*Mus musculus*) IgG1 subtype.

SEQ ID NO:18 shows the amino acid sequence of the heavy chain constant region of mouse (*Mus musculus*) IgG2a subtype.

SEQ ID NO:19 shows the amino acid sequence of the light chain constant region of human (*Homo sapiens*) kappa subtype.

SEQ ID NO:20 shows the amino acid sequence of the light chain constant region of human (*Homo sapiens*) lamda subtype.

SEQ ID NO:21 shows the amino acid sequence of the light chain constant region of mouse (*Mus musculus*) kappa subtype.

SEQ ID NO:22 shows the amino acid sequence of the light chain constant region of mouse (*Mus musculus*) lamda subtype.

SEQ ID NO:23 shows the nucleotide sequence of the primer PmCGR.

SEQ ID NO:24 shows the nucleotide sequence of the primer PmCKR.

SEQ ID NO:25 shows the amino acid sequence of the single chain fragment variable S7A10.

SEQ ID NO:26 shows the amino acid sequence of the single chain fragment variable S8E1.

SEQ ID NO:27 shows the amino acid sequence of the single chain fragment variable S8B8.

SEQ ID NO:28 shows the amino acid sequence of the light chain variable region of the monoclonal antibody H4H8-L1B7.

DETAILED DESCRIPTION OF THE INVENTION

The present inventors have obtained novel antibodies against varicella-zoster virus. In various aspects of the present application, there are provided novel antibodies against varicella-zoster virus, nucleic acid molecules encoding the antibodies or antigen binding fragments thereof, vectors comprising the nucleic acid molecules, host cells comprising the nucleic acid molecules or vectors, a method of preparing and purifying the antibodies, and the medical and biological use of the antibodies. Based on the sequences of the variable regions of the antibodies provided herein, the full-length antibody molecules can be constructed for use as drugs for preventing or treating varicella and herpes zoster.

Unless otherwise indicated, the inventions of the present application can be implemented using conventional molecular biology, microbiology, cell biology, biochemistry, and immunological techniques in the art.

Unless otherwise indicated, the terms used in the present application have the meanings commonly understood by those skilled in the art.

Definitions

As used herein, the term “antibody” refers to an immunoglobulin molecule that is capable of specifically binding to a target via at least one antigen recognition site located in a variable region of the immunoglobulin molecule. Targets include, but are not limited to, carbohydrates, polynucleotides, lipids, and polypeptides, etc. As used herein, an “antibody” includes not only an intact (i.e., full-length) antibody, but also an antigen-binding fragment thereof (e.g., Fab, Fab', $F(ab')_2$, or Fv), a variant thereof, a fusion protein comprising portions of an antibody, a humanized antibody, a chimeric antibody, a diabody, a linear antibody, a single-chain fragment variable, a multi-specific antibody (e.g., a bispecific antibody), and any other modified configurations of an immunoglobulin molecule comprising a desired specific antigen recognition site, including a glycosylated variant of an antibody, an amino acid sequence variant of an antibody, and a covalently modified antibody.

Typically, an intact or full-length antibody comprises two heavy chains and two light chains. Each heavy chain contains a heavy chain variable region (VH) and first, second and third constant regions (CH1, CH2 and CH3). Each light chain contains a light chain variable region (VL) and a constant region (CL). A full-length antibody may be of any type of antibody, such as an IgD, IgE, IgG, IgA, or IgM (or their subtypes) antibody, but not necessarily belongs to any particular type. Immunoglobulins can be assigned to different types depending on their amino acid sequences of the heavy chain constant domains. Generally, immunoglobulins have five main types, i.e., IgA, IgD, IgE, IgG, and IgM, and some of these types can be further classified into subtypes (isotypes), such as IgG1, IgG2, IgG3, IgG4, IgAQ1, and IgA2. Heavy chain constant domains corresponding to individual immunoglobulin types are referred to as a, 6, s, y, and p, respectively. Subunit structures and three-dimensional structures of different types of immunoglobulins are well known.

As used herein, the term "antigen binding fragment" or "antigen-binding portion" refers to a portion or region of an intact antibody molecule responsible for binding an antigen. An antigen binding domain can comprise a heavy chain variable region (VH), a light chain variable region (VL), or both. Each of VH and VL typically contains three complementarity determining regions, i.e., CDR1, CDR2, and CDR3.

It is well known to those skilled in the art that complementarity determining regions (CDRs, usually including CDR1, CDR2 and CDR3) are the regions of a variable region that have mostly impact on the affinity and specificity of an antibody. The CDR amino acid sequences of VH or VL have two common definitions, i.e., the Chothia definition and the Kabat definition (see, e.g., Kabat, "Sequences of Proteins of Immunological Interest", National Institutes of Health, Bethesda, Md. (1991); Al-Lazikani et al., J. Mol. Biol. 273: 927-948 (1997); and Martin et al., Proc. Natl. Acad. Sci. USA 86: 9268-9272 (1989)). For the amino acid sequences of the variable regions of a given antibody, the CDR amino acidsequences in VH and VL amino acid sequences can be determined according to the Chothia definition or the Kabat definition. In an embodiment of the present application, the CDR amino acid sequences are defined according to Kabat.

For the amino acid sequences of the variable regions of a given antibody, the CDR amino acid sequences in the amino acid sequences of variable regions can be determined in a variety of ways, for example, using online software Abysis (http://www.abysis.org/).

Examples of an antigen-binding fragment include, but are not limited to, (1) an Fab fragment, which can be a monovalent fragment having a VL-CL chain and a VH-CHT chain; (2) an $F(ab')_2$ fragment, which can be a divalent fragment having two Fab' fragments linked by a disulfide bridge of the hinge region (i.e., a dimer of Fab'); (3) an Fv fragment having VL and VH domains in a single arm of an antibody; (4) a single-chain Fv (scFv), which can be a single polypeptide chain consisting of a VH domain and a VL domain via a polypeptide linker; and (5) $(scFv)_2$, which can comprise two VH domains linked by a peptide linker and two VL domains that are combined with the two VH domains via a disulfide bridge.

As used herein, the term "specific binding" refers to a non-random binding reaction between two molecules, e.g., binding of an antibody to an antigen epitope.

As used herein, the term "monoclonal antibody" refers to an antibody from a substantially homogeneous antibody population, which means that the antibodies constituting the population are the same except for naturally occurring mutations which may occur in a small number of individual antibodies. Monoclonal antibodies described herein particularly include "chimeric" antibodies in which a portion of the heavy chain and/or the light chain is identical or homologous to a corresponding amino acid sequence in an antibody derived from a particular species or belonging to a particular antibody type or subtype, while the remaining portion of the heavy chain and/or the light chain is identical or homologous to a corresponding amino acid sequence in an antibody derived from another species or belonging to another antibody type or subtype; and also include fragments of such antibodies as long as they are capable of exhibiting the desired biological activity (see, U.S. Pat. No. 4,816,567; and Morrison et al., Proc. Natl. Acad. Sci. USA 81: 6851-6855 (1984)).

In a first aspect, there is provided in the present application an antibody against varicella-zoster virus comprising a heavy chain variable region comprising the amino acid sequences of HCDR1, HCDR2 and HCDR3 and a light chain variable region comprising the amino acid sequences of LCDR1, LCDR2 and LCDR3, wherein the amino acid sequence of HCDR1 is SGNYWN (SEQ ID NO: 29), the amino acid sequence of HCDR2 is YISYDGSTYYNPSLKN (SEQ ID NO: 30), the amino acid sequence of HCDR3 is GYYGYWFAY (SEQ ID NO: 31), the amino acid sequence of LCDR1 is RASSSVSYMH (SEQ ID NO: 32), the amino acid sequence of LCDR2 is ATSNLAS (SEQ ID NO: 33), and the amino acid sequence of LCDR3 is QQWSSNPFT (SEQ ID NO: 34); or the amino acid sequence of HCDR1 is SGYYWN (SEQ ID NO: 54), the amino acid sequence of HCDR2 is YISYDGSNNYNTSLKN (SEQ ID NO: 55), the amino acid sequence of HCDR3 is EDVNYPPYALDY (SEQ ID NO: 35), the amino acid sequence of LCDR1 is RSSQSLVHSNGNTYLH (SEQ ID NO: 36), the amino acid sequence of LCDR2 is KVSNRFS (SEQ ID NO: 37), and the amino acid sequence of LCDR3 is SQSTHVPWT (SEQ ID NO: 38); or the amino acid sequence of HCDR1 is SYTMS (SEQ ID NO: 39), the amino acid sequence of HCDR2 is FISNGGDNNYYADTVKG (SEQ ID NO: 40), the amino acid sequence of HCDR3 is HNGNWGFAY (SEQ ID NO: 41), the amino acid sequence of LCDR1 is SASSSISSNYLH (SEQ ID NO: 42), the amino acid sequence of LCDR2 is RTSNLAS (SEQ ID NO: 43), and the amino acid sequence of LCDR3 is QQGSSIPLT (SEQ ID NO: 44); or the amino acid sequence of HCDR1 is TYAMH (SEQ ID NO: 45), the amino acid sequence of HCDR2 is VISYGGGNRYYAASVKG (SEQ ID NO: 46), the amino acid sequence of HCDR3 is ARDNHYFFGMDV (SEQ ID NO: 47), the amino acid sequence of LCDR1 is RASQGISSWLA (SEQ ID NO: 48), the amino acid sequence of LCDR2 is AASSLQS (SEQ ID NO: 49), and the amino acid sequence of LCDR3 is QQANSFPLT (SEQ ID NO: 50), QEGFYFPIN (SEQ ID NO: 51), QQATYFPIN (SEQ ID NO: 52) or QQSSYFPIA (SEQ ID NO: 53); wherein the amino acid sequences of HCDRs and LCDRs are defined according to Kabat.

In some embodiments of the first aspect, the amino acid sequence of the heavy chain variable region of the antibody is set forth in SEQ ID NO: 1, 3, 5, or 7.

In some embodiments of the first aspect, the amino acid sequence of the light chain variable region of the antibody is set forth in SEQ ID NO: 2, 4, 6, 8, 9, 10, or 28.

In some embodiments of the first aspect, the amino acid sequence of the heavy chain variable region of the antibody is set forth in SEQ ID NO:1, and the amino acid sequence of the light chain variable region of the antibody is set forth in SEQ ID NO:2; or the amino acid sequence of the heavy chain variable region of the antibody is set forth in SEQ ID NO:3, and the amino acid sequence of the light chain variable region of the antibody is set forth in SEQ ID NO:4; or the amino acid sequence of the heavy chain variable region of the antibody is set forth in SEQ ID NO:5, and the amino acid sequence of the light chain variable region of the antibody is set forth in SEQ ID NO:6; the amino acid sequence of the heavy chain variable region of the antibody is set forth in SEQ ID NO:7, and the amino acid sequence of the light chain variable region of the antibody is set forth in SEQ ID NO:8; or the amino acid sequence of the heavy chain variable region of the antibody is set forth in SEQ ID NO:7, and the amino acid sequence of the light chain variable region of the antibody is set forth in SEQ ID NO:9; or the amino acid sequence of the heavy chain variable region of the antibody is set forth in SEQ ID NO:7, and the amino acid sequence of the light chain variable region of the antibody is set forth in SEQ ID NO:10; or the amino acid sequence of the heavy chain variable region of the antibody is set forth in SEQ ID NO:7, and the amino acid sequence of the light chain variable region of the antibody is set forth in SEQ ID NO:28.

In a second aspect, there is provided in the present application an antibody against varicella-zoster virus, wherein the amino acid sequence of the heavy chain variable region of the antibody has at least 90% identity to the amino acid sequence as set forth in any one of SEQ ID NOs: 1, 3, 5, and 7, and the amino acid sequence of the light chain variable region of the antibody has at least 90% identity to the amino acid sequence as set forth in any one of SEQ ID NOs: 2, 4, 6, 8, 9, 10, and 28.

In some embodiments of the second aspect, the amino acid sequence of the heavy chain variable region of the antibody has at least 90%, 91%, 92%, 93%, 94%, 95%, 96%, 97%, 98%, 99% or more homology to the amino acid sequence as set forth in any one of SEQ ID NOs: 1, 3, 5, and 7.

In some embodiments of the second aspect, the amino acid sequence of the light chain variable region of the antibody has at least 90%, 91%, 92%, 93%, 94%, 95%, 96%, 97%, 98%, 99%, or more homology to the amino acid sequence as set forth in any one of SEQ ID NOs: 2, 4, 6, 8, 9, 10, and 28.

In some embodiments of the second aspect, the amino acid sequence of the heavy chain variable region of the antibody differs from the amino acid sequence as set forth in any one of SEQ ID NOs: 1, 3, 5, and 7 by about 1, 2, 3, 4, 5, 6, 7, 8, 9, or 10 amino acid substitutions, deletions, and/or additions.

In some embodiments of the second aspect, the amino acid sequence of the light chain variable region of the antibody differs from the amino acid sequence as set forth in any one of SEQ ID NOs: 2, 4, 6, 8, 9, 10, and 28 by about 1, 2, 3, 4, 5, 6, 7, 8, 9, or 10 amino acid substitutions, deletions, and/or additions.

In some embodiments of the second aspect, the C-terminal or N-terminal region of the amino acid sequence as set forth in any one of SEQ ID NOs: 1, 3, 5, and 7 can also be truncated by about 1, 2, 3, 4, 5, 6, 7, 8, 9, 10, 11, 12, 13, 14, 15, 20, 25 or more amino acids while still retaining the function similar to that of the heavy chain variable region of the antibody.

In some embodiments of the second aspect, 1, 2, 3, 4, 5, 6, 7, 8, 9, 10, 11, 12, 13, 14, 15, 20, 25 or more amino acids can also be added to the C-terminal or N-terminal region of the amino acid sequence as set forth in any one of SEQ ID NOs: 1, 3, 5, and 7, and the resulting amino acid sequences still retain the function similar to that of the heavy chain variable region of the antibody.

In some embodiments of the second aspect, 1, 2, 3, 4, 5, 6, 7, 8, 9, 10, 11, 12, 13, 14, 15, 20, 25 or more amino acids can also be added or deleted at a region other than the C-terminus or the N-terminus of the amino acid sequence as set forth in any one of SEQ ID NOs: 1, 3, 5, and 7, provided that the altered amino acid sequences substantially retain the function similar to that of the heavy chain variable region of the antibody.

In some embodiments of the second aspect, the C-terminal or N-terminal region of the amino acid sequence as set forth in any one of SEQ ID NOs: 2, 4, 6, 8, 9, 10, and 28 can also be truncated by about 1, 2, 3, 4, 5, 6, 7, 8, 9, 10, 11, 12, 13, 14, 15, 20, 25 or more amino acids while still retaining the function similar to that of the light chain variable region of the antibody.

In some embodiments of the second aspect, 1, 2, 3, 4, 5, 6, 7, 8, 9, 10, 11, 12, 13, 14, 15, 20, 25 or more amino acids can also be added to the C-terminal or N-terminal region of the amino acid sequence as set forth in any one of SEQ ID NOs: 2, 4, 6, 8, 9, 10, and 28, and the resulting amino acid sequences still retain the function similar to that of the light chain variable region of the antibody.

In some embodiments of the second aspect, 1, 2, 3, 4, 5, 6, 7, 8, 9, 10, 11, 12, 13, 14, 15, 20, 25 or more amino acids can also be added or deleted at a region other than the C-terminus or the N-terminus of the amino acid sequence as set forth in any one of SEQ ID NOs: 2, 4, 6, 8, 9, 10, and 28, provided that the altered amino acid sequences substantially retain the function similar to that of the light chain variable region of the antibody.

In some embodiments of the first and second aspects, the antibody is a whole antibody, a Fab fragment, a $F(ab')_2$ fragment, or a single chain Fv (scFv).

In some embodiments of the first and second aspects, the antibody is a whole human antibody.

In some embodiments of the first and second aspects, the antibody is a monoclonal antibody.

In some embodiments of the first and second aspects, the antibody further comprises a heavy chain constant region selected from an IgG1 subtype, an IgG2 subtype, or an IgG4 subtype.

In some specific embodiments of the first and second aspects, the heavy chain constant region is an IgG1 subtype.

In some embodiments of the first aspect and the second aspect, the antibody further comprises a light chain constant region selected from a kappa subtype or a lamda subtype.

In some specific embodiments of the first aspect and the second aspect, the light chain constant region is a kappa subtype.

In some embodiments of the first and second aspects, the antibody binds to the gH/gL protein of varicella-zoster virus; and/or the antibody mediates antibody-dependent cell-mediated cytotoxicity (ADCC).

In a third aspect, there is provided in the present application a nucleic acid molecule encoding the antibody of the first or second aspect.

In some embodiments, the nucleic acid molecule is operably linked to a regulatory nucleotide sequence that can be recognized by a host cell transformed with the vector.

In a fourth aspect, there is provided in the present application a pharmaceutical composition comprising the antibody of the first or second aspect, and a pharmaceutically acceptable excipient, diluent, or carrier.

In some embodiments, the pharmaceutical composition is used for preventing or treating varicella and herpes zoster.

In some embodiments, the pharmaceutical composition can further comprise one or more of a lubricant, such as talc, magnesium stearate, and mineral oil; a wetting agent; an emulsifier; a suspending agent; a preservative such as benzoic acid, sorbic acid and calcium propionate; a sweetening agent and/or a flavoring agent.

In some embodiments, the pharmaceutical composition herein can be formulated as a tablet, a pill, a powder, a lozenge, an elixir, a suspension, an emulsion, a solution, a syrup, a suppository, or a capsule.

In some embodiments, the pharmaceutical composition of the present application can be delivered using any physiologically acceptable administration route including, but not limited to, oral administration, parenteral administration, nasal administration, rectal administration, intraperitoneal administration, intravascular injection, subcutaneous administration, transdermal administration, or inhalation administration.

In some embodiments, a pharmaceutical composition for therapeutic use can be formulated for storage in the form of a lyophilized formulation or an aqueous solution by mixing an agent with desired purity with a pharmaceutically acceptable carrier or excipient where appropriate.

In a fifth aspect, there is provided in the present application use of the antibody of the first or second aspect, the nucleic acid molecule of the third aspect, or the pharmaceutical composition of the fourth aspect in the manufacture of a medicament for the prevention or treatment of varicella and herpes zoster.

In a sixth aspect, there is provided in the present application a method of preventing or treating varicella and herpes zoster, comprising administering to a subject in need thereof the antibody of the first or second aspect, or the pharmaceutical composition of the fourth aspect.

In other aspects, there is also provided in the present application an isolated nucleic acid molecule encoding the antibody or the light or heavy chain thereof of the present invention, as well as a vector comprising the nucleic acid molecule, a host cell comprising the vector, and a method of producing the antibody. In some embodiments, the nucleic acid molecule is operably linked to a regulatory nucleotide sequence that can be recognized by a host cell transformed with the vector. In some embodiments, the method of producing the antibody includes culturing the host cell to facilitate expression of the nucleic acid. In some embodiments, the method of producing the antibody further comprises recovering the antibody from the host cell culture medium.

In addition, the antibody specific for varicella-zoster virus described herein can also be used to detect the presence of varicella-zoster virus in a biological sample. Antibody-based detection methods are well known in the art and include, for example, ELISA, immunoblot, radioimmunoassay, immunofluorescence, immunoprecipitation, and other related techniques.

It is to be understood that the foregoing detailed description is intended only to enable those skilled in the art to have better understanding of the present application and is not intended to cause limitations in any way. Various modifications and variations can be made to the described embodiments by those skilled in the art.

EXAMPLES

The following Examples are for purposes of illustration only and are not intended to limit the scope of the present application.

Example 1: Preparation of the Recombinant Proteins

The gH glycoprotein (SEQ ID NO:11) and gL glycoprotein (SEQ ID NO:12) are needed in the preparation and identification of an antibody specific for varicella-zoster virus. gH and gL can only be efficiently secreted and expressed after they are separately synthesized in cells and undergo folding together to form a gH/gL dimer. There are a large number of post-translational modifications (e.g., glycosylation or disulfide bonds, etc) in the gH/gL dimer. Therefore, the use of the mammal cell expression system would be more favorable for maintaining the structure and function of the recombinant proteins. Meanwhile, the addition of the His tag (His, SEQ ID NO:13) to the C-terminus of the gH glycoprotein will be more favorable for the purification of the recombinant proteins and the identification of the monoclonal antibody functions. Genes encoding the gH recombinant protein (comprising His tags) and the gL recombinant protein were designed and synthesized according to the amino acid sequences of the gH and gL glycoproteins of the varicella-zoster virus strain Oka from the Uniprot database. The synthetic genes encoding the gH-His and gL recombinant proteins were cloned into suitable eukaryotic expression vectors (such as pcDNA3.1, Invitrogen Inc., etc) using conventional molecular biology techniques, respectively, and the prepared recombinant protein expression plasmids were then transfected into HEK293 cells (such as HEK293F, Invitrogen Inc.) using liposomes (such as 293fectin, Invitrogen Inc., etc) or other transfection reagents (such as PEI, etc). The cells were cultured in suspension in serum-free media for 3-5 days. The culture supernatant was then harvested by centrifugation. The recombinant protein in the supernatant was subjected to one-step purifcation using a metal chelate affinity chromatography column (such as HisTrap FF, GE Inc., etc). The recombinant protein preservation buffer was then replaced with PBS (pH 7.0) or other suitable buffers using a desalting column (such as Hitrap desaulting, GE Inc., etc). If necessary, the sample can be sterilized by filtration and then stored in aliquots at −20° C.

In the preparation of the recombinant antibody, the heavy chain constant region of the antibody can be a human IgG1 subtype (SEQ ID NO:14), a human IgG2 subtype (SEQ ID NO: 15), a human IgG4 subtype (SEQ ID NO:16), or a mouse IgG1 subtype (SEQ ID NO:17), a mouse IgG2a (SEQ ID NO:18) subtype, and the light chain constant region can be a human κ subtype (SEQ ID NO:19), a human k subtype (SEQ ID NO:20), a mouse κ subtype (SEQ ID NO:21), or a mouse k subtype (SEQ ID NO: 22). The nucleotide sequences encoding the heavy chain variable region and the light chain variable region of the antibody were cloned into eukaryotic expression vectors (such as pcDNA3.1, Invitrogen Inc.) fused with the nucleotide sequences encoding the heavy chain constant region and the light chain constant region, respectively, by conventional molecular biological means, and the whole antibody was expressed in combination. The prepared recombinant antibody expression plasmids were then transfected into HEK293 cells (such as HEK293F, Invitrogen Inc.) using liposomes (such as 293fectin, Invitrogen, Inc., etc) or other transfection reagents (such as PEI, etc). The cells were cultured in suspension in serum-free mediums for 3-5 days. The culture supernatant was then harvested by centrifugation. The recombinant antibody in the supernatant was subjected to one-step purification using Protein A/G affinity chromatography column (such as HisTrap FF, GE Inc, etc). The recombinant protein preservation buffer was then replaced with PBS (pH 7.0) or other suitable buffers using a desalting column (such as Hitrap desaulting, GE Inc., etc). If necessary, the sample can be sterilized by filtration and then stored in aliquots at −20° C.

Example 2: Screening of the Mouse Monoclonal Antibodies Against the Varicella-Zoster Virus Recombinant Protein gH/gL 2.1 Mouse Immunization and Preparation of Immune Antibody Library Recombinant protein gH-His/gL prepared in Example 1 was used as an antigen to immunize 6-8 weeks old of BALB/c mice at a dose of 50 pg/mouse, with booster immunization every 14 days. The mice were sacrificed 8 weeks after the initial immunization, and splenocytes were collected. Mouse spleen lymphocytes were isolated using a mouse lymphocyte isolation solution (Dakewe Biotech Co., Ltd., CAT #DKW33-R0100). Total RNA was extracted from the isolated lymphocytes using a cellular total RNA extraction kit (Tiangen Biotech (Beijing) Co., Ltd., CAT #DP430). Using the extracted total RNA as a template, cDNAs of the heavy chain variable region and light chain variable region of the antibody were synthesized using a first strand cDNA synthesis kit (Thermo scientific, CAT #K1621), respectively. Gene-specific primers were used as reverse transcription primers. The primer pairing regions were located in the heavy chain constant region and light chain constant region of the antibody, respectively, and the specific sequences were PmCGR: TGCATTTGAACTCCTTGCC (SEQ ID NO:23) and PmCKR: CCATCAATCTTCCACTTGAC (SEQ ID NO:24), respectively. The synthesized cDNAs were immediately stored at −70° C. for later use. Then, using the cDNA obtained by reverse transcription as a template, the primers were synthesized by referring to the reference (Krebber A, Bornhauser S, Burmester J, et al., Reliable cloning of functional antibody variable domains from hybridomas and spleen cell repertoires employing a reengineered phage display system. *J Immunol Methods.* 1997; 201(1):35-55, which is incorporated by reference in its entirety). The nucleotide sequences encoding VH and VK of the mouse antibodies were amplified by PCR, respectively. Then, the single chain fragment variable (scFv) was constructed by overlapping extension PCR technology. Finally, the prepared nucleotide sequences encoding the mouse single chain fragment variable were cloned into the vector pADSCFV-S (see Example 1 of the Chinese Patent Application No. 201510097117.0 for detailed experimental protocols, which is incorporated by reference in its entirety) to construct a scFv library. The antibody library has a capacity of 2.13E+08, and an accuracy of 50%.

2.2 Screening of the Mouse Single Chain Fragment Variables Against the Varicella-Zoster Virus Recombinant Protein gH/gL Referring to the reference (see the Chinese Patent Application No. 201510097117.0 for detailed experimental protocols, which is incorporated by reference in its entirety), the above constructed phage library displaying the mouse single chain fragment variable was screened by a solid phase screening strategy (as for the experimental protocol, see, Phage Display: A Practical Approach, Clackson, T. (USA) and Lowman, H. B. (USA) (ed.), translated by Lan Ma et al., Chemical Industry Press, May 2008, which is incorporated by reference in its entirety) using the recombinant protein gH-His/gL prepared in Example 1 as an antigen. Three rounds of screening were carried out by means of binding, elution, neutralization, infection and amplification. Finally, a number of single chain fragment variables were obtained, which have different sequences, but can specifically bind to the recombinant protein gH-His/gL, including clones S7A10 (the amino acid sequence of which is set forth in SEQ ID NO:25), S8E1 (the amino acid sequence of which is set forth in SEQ ID NO:26) and S8B8 (the amino acid sequence of which is set forth in SEQ ID NO:27).

Example 3: Affinity Analysis of the Mouse Monoclonal Antibodies Against the Varicella-Zoster Virus Recombinant Protein gH/gL The nucleotide sequences encoding the light and heavy chains of the single chain fragment variable that specifically bind to gH/gL were cloned into a eukaryotic expression vector using conventional molecular biological methods so as to prepare a recombinant human IgG1-κ version of the mouse-human chimeric antibody.

The affinity of the anti-gH/gL antibody was determined by the surface plasmon resonance technique using Biacore ×100. Reagents and consumables such as an amino-coupling kit (BR-1000-50), a human antibody capture kit (BR-1008-39), a CM5 chip (BR100012) and 10×HBS-EP (pH 7.4, BR100669) were purchased from GE healthcare. The surface of the carboxylated CM5 chip was activated with 1-ethyl-3-(3-dimethylaminopropyl) carbodiimide hydrochlorid (EDC) and N-Hydroxysuccinimide (NHS) according to the instructions in the kit. An anti-human IgG (Fc) antibody (capture antibody) was diluted to 25 μg/mL with 10 mM sodium acetate (pH5.0), and then injected at a flow rate of 10 μL/min to achieve a coupling amount of approximately up to 10,000 response units (RU). After injection of the capture antibody, 1 M ethanolamine was injected to block unreacted groups. For the kinetics measurement, the anti-gH/gL antibody was diluted to 0.5-1 μg/mL, and injected at 10 μL/min to ensure that approximately 50RU of the antibody was captured by the anti-human Fc antibody. Recombinant protein gH/gL was then set to a series of concentration gradients (e.g., 1.23 nM, 3.7 nM, 11.1 nM, 33.3 nM and 100 nM) and injected at 25° C. from lower to higher concentrations at 30 μL/min, with an association time of 120 s and a dissociation time of 3,600 s. A 3M $MgCl_2$ solution was injected at 10 μL/min for 30 s to regenerate the surface of the chip. The association rate ($K_a$) and dissociation rate ($K_d$) were calculated by fitting the binding and dissociation sensing grams with a 1:1 binding model using Biacore ×100 evaluation software version 2.0.1. The dissociation equilibrium constant ($K_D$) was calculated as the ratio Kd/Ka. The fitting results were shown in Table 1.

TABLE 1

Affinity constants for the binding of the recombinant monoclonal antibodies against the varicella-zoster virus recombinant protein gH/gL to the varicella-zoster virus recombinant protein gH/gL

| | $K_a$ | $K_d$ | $K_D$ |
|---|---|---|---|
| S8B8-IgG1 | 4.488E+5 | 2.068E−4 | 4.609E−10 |
| S7A10-IgG1 | 1.721E+5 | 9.531E−4 | 5.539E−9 |
| S8E1-IgG1 | 6.695E+4 | 2.995E−4 | 4.473E−9 |

Example 4: Epitope Analysis of the Mouse Monoclonal Antibodies Against the Varicella-Zoster Virus Recombinant Protein gH/gL 96-well ELISAplates were coated with the varicella-zoster virus recombinant protein gH/gL (3 μg/mL, 100 μL/well) overnight in a refrigerator at 4° C., and were then blocked with a blocking solution (PBS-0.1% Tween 20-3% milk) at 37° C. for 1 hour. Gradient dilutions of anti-recombinant protein gH/gL antibodies (i.e. S7A10, S8B8 and S8E1) were performed with each of the purified anti-recombinant protein gH/gL phages (i.e., S7A10, S8B8 and S8E1) at a fixed concentration ($5\times10^{10}$-$1\times10^{11}$ cfu/mL), respectively. The starting concentration of the antibodies was 10 μg/mL, and the dilution was carried out at 3-fold for a total of 8-10 concentration gradients. The antibody dilutions were added to the blocked 96-well ELISA plates at 100 μL/well and the plates were incubated at 37° C. for 1 hour. Then, the ELISA plates were washed with PBS-0.1% Tween 20, followed by the addition of HRP-anti-M13 secondary antibody (Sino Biological Inc., 11973-MM05T-H) and the plates were incubated at 37° C. for 1 hour. The ELISA plates were washed with PBS-0.1% Tween 20, and an OPD substrate chromogenic solution was added. After incubation for 5-10 minutes, the color development was terminated with 1M $H_2SO_4$. The optical density values were measured using a microplate reader at 492 nm/630 nm dual wavelength. The results of ELISA assay were shown in FIGS. 1A-IC. The monoclonal antibody S8E1-IgG1 could not block the binding of phages S8B8 and S7A10 to the recombinant protein gH/gL (FIG. 1A). The monoclonal antibody S8B8-IgG1 could partially block the binding signal of the phage S8E1 to the recombinant protein gH/gL, but had no effect on the binding of the phage S7A10 to the recombinant protein gH/gL (FIG. 1B). The monoclonal antibody S7A10-IgG1 could not block the binding of the phages S8B8 and S7A10 to the recombinant protein gH/gL (FIG. 1C).

Example 5: Neutralization Activity of the Mouse Monoclonal Antibodies Against the Varicella-Zoster Virus Recombinant Protein gH/gL Neutralization activity of the antibodies (S7A10, S8B8 and S8E1) was determined by a reduction of plaque formation in MRC5 cells infected with a mixture of an antibody and VZV. MRC-5 cells were seeded in 6-well cell culture plates at a density of $1.5\times10^5$ cells/well and cultured for 72 hours to form monolayer cells. At 90% confluence, the culture supernatant was removed and a virus maintenance solution (i.e., MEM medium containing 2% serum) was added at 400 μL per well. VZV (Oka) was diluted to 2,000 pfu/mL with the virus maintenance solution. That is, after the virus maintenance solution was mixed with the antibody in equal volume, every 100 μL mixed solution comprised 100 pfu VZV. The antibody was diluted by a 2-fold gradient with a viral dilution. The starting concentration of the antibodies was 20 μg/mL, and there were 8 concentration gradients. That is, after mixing with an equal volume of VZV, the concentrations of the antibody were 10 μg/mL, 5 μg/mL, 2.5 μg/mL, 1.25 μg/mL, 0.62 μg/mL, 0.31 μg/mL, 0.16 μg/mL and 0.08 μg/mL. VZV was mixed with the antibody in equal volume and left to stand at 25° C. for 1 hour to infect MRC5 cells in 6-well plates (100 μL/well). After adsorption at 37° C. for 1 hour, the supernatant was pipetted and discarded. The plate was washed twice with PBS. 3 mL of maintenance solution was added to each well, and the culture was maintained and cultured at 37° C. for 8 days. Then the supernatant was discarded. The plates were washed once with PBS. 1 mL of Coomassie Brilliant Blue staining solution was added to each well. After 10 minutes, the plates were washed once with PBS, and were placed in a bright place to count plaque. The concentration of the antibody for 50% reduction in plaque (PRNT50) was calculated by Reed and Muench method. The experimental results were shown in Table 2.

TABLE 2

Neutralization activity of the mouse monoclonal antibodies against the varicella-zoster virus recombinant protein gH/gL

| Antibody | S7A10 | S8B8 | S8E1 |
|---|---|---|---|
| PRNT50 (μg/mL) | 0.34 | 0.38 | 0.38 |

Example 6: Activity of the Monoclonal Antibodies Against the Varicella-Zoster Virus Recombinant Protein gH/gL in Inhibiting Virus Transmission Between Cells Antibodies (S7A10, S8B8 and S8E1) were added 24 hours after MRC5 cells were infected by VZV. The activity of the antibodies in inhibiting virus transmission between cells was determined by a reduction of plaque formation. MRC-5 cells were seeded in 6-well cell culture plates at a density of $1.5\times10^5$ cells/well, and cultured for 72 hours to form monolayer cells. At 90% confluence, the culture supernatant was removed and a virus maintenance solution (i.e., MEM medium containing 2% serum) was added to each well at 400 μL. VZV was diluted to 1,000 pfu/mL with the virus maintenance solution to infect MRC5 cells in 6-well cell culture plates (100 μL/well). That is, cells in each well were infected with 100 pfu of VZV. After adsorption at 37° C. for 1 hour, the supernatant was pipetted and discarded. The plates were washed twice with PBS. 3 mL of maintenance solution was added to each well, and the culture was maintained and cultured at 37° C. for 24 hours. The antibody was diluted by a 2-fold gradient with a viral dilution. The starting concentration of the antibody was 400 μg/mL, and there were 8 concentration gradients. The antibody was added to MRC5 cells infected with VZV in 6 well plates (30 μL/well). That is, the concentrations of the antibody in the culture solutions were 4 μg/mL, 2 μg/mL, 1 μg/mL, 0.5 μg/mL, 0.25 μg/mL and 0.125 μg/mL. The culture was maintained and cultured at 37° C. for 8 days. The supernatant was discarded.

The plates were washed once with PBS. 1 mL of Coomassie Brilliant Blue staining solution was added to each well. After 10 minutes, the plates were washed once with PBS, and were placed in a bright place to count plaque. The concentration of the antibody for 50% reduction in plaque was calculated. The experimental results were shown in Table 3.

TABLE 3

Activity of the mouse monoclonal antibodies against the varicella-zoster virus recombinant protein gH/gL in inhibiting virus transmission between cells

| Antibody | S7A10 | S8B8 | S8E1 |
|---|---|---|---|
| PRNT50(μg/mL) | 0.93 | 3.21 | 2.82 |

Example 7: Screening of the Fully Human Monoclonal Antibody Against the Varicella-Zoster Virus Recombinant Protein gH/gL A natural human phage antibody library was screened by a solid phase screening strategy (as for the experimental protocol, see, Phage Display: A Practical Approach, Clackson, T. (USA) and Lowman, H. B. (USA) (ed.), translated by Lan Ma et al., Chemical Industry Press, May 2008, which is incorporated by reference in its entirety) using the recombinant protein gH-His/gL prepared in Example 1 as an antigen (see Example 1 in the Chinese Patent Application No. 201510097117.0 for detailed experimental protocols, which is incorporated by reference in its entirety). Finally, a fully human single chain fragment variable H4H8-L1B7 was obtained, which specifically binds to the recombinant protein gH-His/gL

Example 8: Epitope Analysis of the Fully Human Monoclonal Antibody Against the Varicella-Zoster Virus Recombinant Protein gH/gL The nucleotide sequences encoding the light and heavy chains of H4H8-L1B7 were cloned into a eukaryotic expression vector using conventional molecular biological methods so as to prepare a recombinant human IgG1-κ version of the fully human monoclonal antibody.

Figure 2:
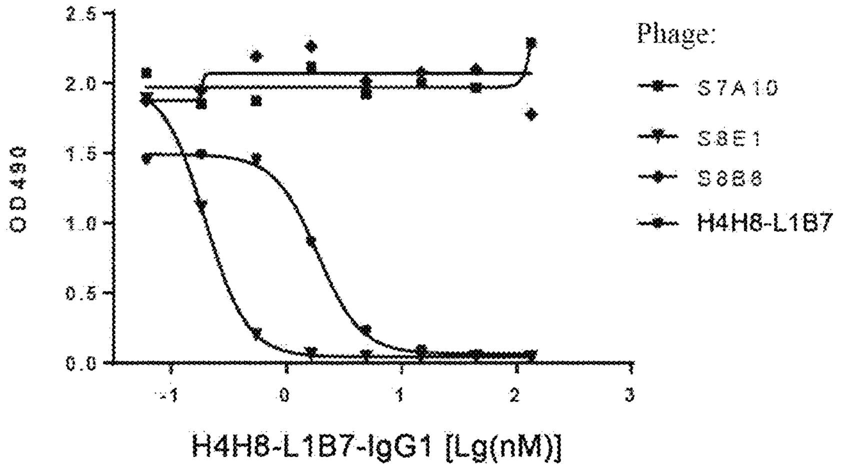
FIG. 2 shows the result from an ELISA assay assessing the ability of the monoclonal antibody H4H8-L1B7 against the varicella-zoster virus recombinant protein gH/gL to block the binding of purified anti-recombinant protein gH/gL phages to the recombinant protein gH/gL.

Referring to Example 4, gradient dilution of the anti-recombinant protein gH/gL antibody (i.e., H4H8-L1B7-IgG1) was performed with each of the purified anti-recombinant protein gH/gL phages (i.e., S7A10, S8E1, S8B8 and H4H8-L1B7) at a fixed concentration ($5\times10^{10}$-$1\times10^{11}$ cfu/mL), respectively. The blockage of the binding of the anti-recombinant protein gH/gL phages to the recombinant protein gH/gL by the human monoclonal antibody H4H8-LTB7-IgG1 against the recombinant protein gH/gLwas determined. The results of the ELISA assay were shown in FIG. 2. The monoclonal antibody H4H8-L1B7-IgG1 could completely block the binding signals of the phages H4H8-L1B7 and S8E1 to the recombinant protein gH/gL, and has no effect on the binding signals of the other two phages (S7A10 and S8B8) to the recombinant protein gH/gL.

Example 9: Construction and Screening of the Light Chain Mutation Library of the Fully Human Monoclonal Antibody H4H8-L1B7 Against the Varicella-Zoster Virus Recombinant Protein gH/gL 9.1 Construction and Screening of H4H8-L1B7 Light Chain Mutation Library The in vitro affinity maturation of the H4H8-L1B7 monoclonal antibody was performed using a light chain CDR mutation strategy based on a dual-vector phage display system (see Example 5 in Chinese Patent No. 201510097117.0 previously submitted by the applicant for the specific manipulation, which is incorporated by reference in its entirety). An LCDR3 mutation library with a library capacity of more than 5.5E+07 was constructed using the classical overlap extension PCR method. The design scheme of the mutation library was shown in Table 4.

TABLE 4

The design scheme of the LCDR3 mutation library

| Initial amino acid | Mutant amino acid | Degenerate code |
|---|---|---|
| Q | Q, E, L, V, R or G | SDG |
| Q | Q, E, L, V, R or G | SDG |
| A | G, V, A, D, I, T, N or S | RNT |
| N | F, I, S, T, Y or N | WHT |
| N | F, I, S, T, Y or N | WHT |
| F | F, I, S, T, Y or N | WHT |
| P | F, S, L, P, A or V | BYC |
| L | L, S, I, T, A or V | DYC |
| T | S, T, A, Y, N or D | DMT |

The LCDR3 mutation library of L1B7 (SEQ ID NO:28) was subjected to 2 rounds of screening by a solid-phase screening strategy using the recombinant protein gH-His/gL as an antigen and on the basis of the heavy chain of H4H8-L1B7. Finally, three light chain mutants, L13C1(SEQ ID NO:8), L13C7(SEQ ID NO:9) and L14H8(SEQ ID NO:10) were obtained.

9.2 Affinity Analysis of the Light Chain Mutants of H4H8-L1B7

The nucleotide sequences encoding the light and heavy chains of H4H8-L14H8, H4H8-L13C1 and H4H8-L13C7 were cloned into eukaryotic expression vectors using conventional molecular biological methods so as to prepare the recombinant human IgG1-κ versions of the fully human monoclonal antibodies.

Referring to Example 3, the affinity of the light chain mutants of H4H8-L1B7 was analyzed using Biacore ×100 evaluation software version 2.0.1. The results were shown in Table 5.

TABLE 5

Affinity constants for the binding of the light chain mutants of H4H8-L1B7 to the recombinant protein gH/gL

| | $K_a$ | $K_d$ | $K_D$ |
|---|---|---|---|
| H4H8-L13C1-IgG1 | 2.601E+5 | 1.281E−4 | 4.925E−10 |
| H4H8-L13C7-IgG1 | 2.494E+5 | 1.211E−4 | 4.855E−10 |
| H4H8-L14H8-IgG1 | 3.666E+5 | 1.062E−4 | 2.896E−10 |

Example 10: Neutralization Activity of the Monoclonal Antibodies Against the Varicella-Zoster Virus Recombinant Protein gH/gL Referring to Example 5, the neutralization activity of the monoclonal antibodies H4H8-L14H8, H4H8-L13C1 and H4H8-L13C7 was determined. The experimental results were shown in Table 6.

TABLE 6

Neutralization activity of the monoclonal antibodies against the varicella-zoster virus recombinant protein gH/gL

| | H4H8-L14H8 | H4H8-L13C1 | H4H8-L13C7 |
|---|---|---|---|
| PRNT50(μg/mL) | 0.016 | 0.016 | >0.4 |

Example 11: Activity of the Monoclonal Antibodies Against the Varicella-Zoster Virus Recombinant Protein gH/gL in Inhibiting Virus Transmission Between Cells Referring to Example 6, the activity of the monoclonal antibodies H4H8-L14H8, H4H8-L13C1 and H4H8-L13C7 in inhibiting virus transmission between cells was determined. The experimental results were shown in Table 7.

TABLE 7

Activity of the monoclonal antibodies against the varicella-zoster virus recombinant protein gH/gL in inhibiting virus transmission between cells

| | H4H8-L14H8 | H4H8-L13C1 | H4H8-L13C7 |
|---|---|---|---|
| PRNT50(μg/mL) | 0.31 | 0.28 | >2 |

Figure 3:
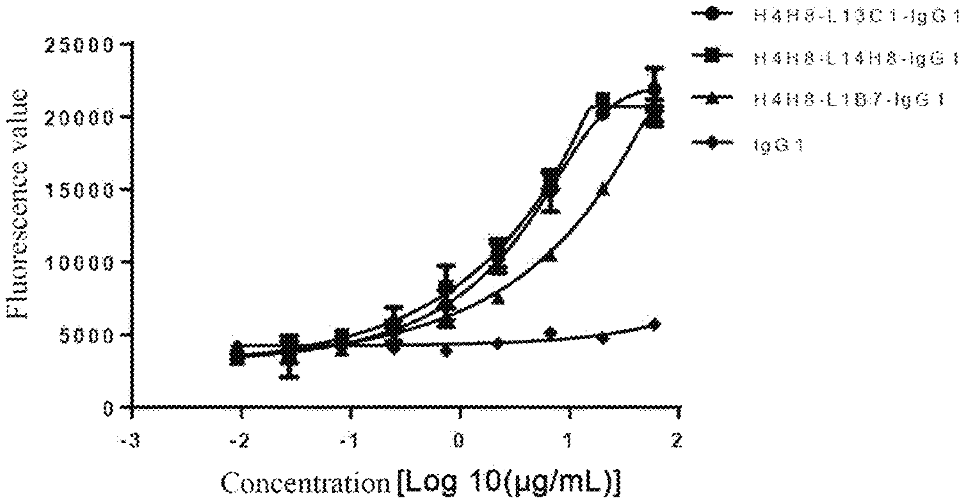
FIG. 3 shows the results assessing the ADCC activities of the anti-varicella-zoster virus monoclonal antibodies using Jurkat-Dual-CD16a reporter cells.

Example 12: Anti-Varicella-Zoster Virus Monoclonal Antibodies Mediate ADCC Effects on the Infected Cells The present inventors constructed a Jurkat-Dual-CD16a reporter gene cell strain by transforming CD16a plasmid into Jurkat-dual cells purchased from Invivogen Inc. When an antibody-dependent cell-mediated cytotoxicity (ADCC) effect occurrs, the activation signal was transferred to the downstream NF-κB pathway through the CD16a molecule. ADCC activity was finally detected by luciferase. 90% confluent MRC5 cells in a T75 cell culture flask were infected by varicella-zoster virus (VZV) at MOI=0.01. The cells were observed under a microscope. When 50%-60% of the cells in the flask were diseased (96 hours after infection), the cells were subjected to trypsinization and harvested. Jurkat-Dual-CD16a cells and target cells infected with VZV (MRC-5 cells) were mixed in the effector-to-target ratio of 15:1. The dilutions of the molecules to be tested H4H8-L14H8-IgG1, H4H8-L13C1-IgG1, H4H8-L1B7-IgG1 and the isotype control IgG1 antibody were all started at a final concentration of 60 μg/mL, with a 3-fold dilution for a total of 10 concentration points. The diluted antibodies were co-cultured with the above mixed cells, respectively. After incubation for 20 h, the mixture was centrifuged and 50 μL supernatant was taken. An automatic loading program was set in a microplate reader. 50 μL luciferase detection solution quanti-luc (Invivogen Inc., Cat. No. rep-qlc2) was added to each well and the fluorescence intensity was measured by a full wavelength detection. The results of ADCC activity based on Jurkat-Dual-CD16a reporter gene system showed that H4H8-L14H8-IgG1 and H4H8-L13C1-IgG1 had better ADCC activity than H4H8-L1B7-IgG1 (FIG. 3).

Exemplary embodiments of the inventions of the present applicationhave been described above. However, those skilled in the art can modify or improve the exemplary embodiments described herein without departing from the spirit and scope of the present application, and variations or equivalents derived therefrom also fall within the scope of the present application.

REFERENCE

Davison, A. J., and J. E. Scott. 1986. The complete DNA sequence of varicella-zoster virus. J. Gen. Virol. 67:1759-1816.

Davison, A. J., C. M. Edson, R. W Ellis, B. Forghani, D. Gilden, C. Grose, P. M. Keller, A. Vafai, Z. Wroblewska, and K. Yamanishi. 1986. A new common nomenclature for the glycoprotein genes of varicella-zoster virus and their glycosylated products. J. Virol. 57:1195-1197.

Kapsenberk, J. G. 1964. Possible antigenic relationship between varicellazoster virus and herpes simplex virus. Arch. Ges. Virusforsch. 15:67-73.

Forghani, B., L. Ni, and C. Grose. 1994. Neutralization epitope of the varicella-zoster virus gH:gL glycoprotein complex. Virology 199:458-462.

Zhu, Z., M. D. Gershon, R. Ambron, C. Gabel, and A. A. Gershon. 1995. Infection of cells by varicella-zoster virus: inhibition of viral entry by mannose 6-phosphate and heparin. Proc. Natl. Acad. Sci. USA 92:3546-3550.

Sadzot-Delvaux, C., M. P. Merville-Louis, P. Delree, P. Marc, J. Piette, G. Moonen, and B. Rentier. 1990. An in vivo model of varicella-zoster virus latent infection of dorsal root ganglia. J. Neurosci. Res. 26:83-89.

Gershon, A. A., S. P. Steinberg, and L. Gelb. 1984. Clinical reinfection with varicella-zoster virus. J. Infect. Dis. 149: 137-142.

Guess, H. A., D. D. Broughton, L. J. Melton, and L. T. Kurland. 1985. Epidemiology of herpes zoster in children and adolescents: a populationbased study. Pediatrics 76:512-518.

Bogger-Goren, S., J. M. Bernstein, A. A. Gershon, and P. L. Ogra. 1984. Mucosal cell-mediated immunity to varicella-zoster virus: role in protection against disease. J. Pediatr. 105:195-199

Zaia, J. A., M. J. Levin, S. R. Preblud, J. Leszczynski, G. G. Wright, R. J. Ellis, A. C. Curtis, M. A. Valerio, and J. LeGore. 1983. Evaluation of varicella-zoster immune globulin: protection of immunosuppressed children after household exposure to varicella. J. Infect. Dis. 147:737-743.

Gershon, A. A.; Steinberg, S.; Gelb, L.; NIAID-Collaborative-Varicella-Vaccine-Study-Group. Live attenuated varicella vaccine: Efficacy for children with leukemia in remission. JAMA 1984, 252, 355-362.

Chen, J.; Gershon, A.; Silverstein, S. J.; Li, Z. S.; Lungu, O.; Gershon, M. D. Latent and lytic infection of isolated guinea pig enteric and dorsal root ganglia by varicella-zoster virus. J. Med. Virol. 2003, 70, S71-S78.

Oxman, M. N.; Levin, M. J.; Johnson, G. R.; Schmader, K. E.; Straus, S. E.; Gelb, L. D.; Arbeit, R. D.; Simberkoff, M.; Gershon, A.; Davis, L. E.; et al. Avaccine to prevent herpes zoster and postherpetic neuralgia in older adults. N. Engl. J. Med. 2005, 352, 2271-2284.

Cunningham, A. L.; Lal, H.; Kovac, M.; Chlibek, R.; Hwang, S. J.; Diez-Domingo, J.; Godeaux, O.; Levin, M.; McElhaney, J. E.; Puig-Barbera, J.; et al. Efficacy of the Herpes Zoster Subunit Vaccine in Adults 70 Years of Age or Older. N. Engl. J. Med. 2016, 375, 1019-1032.

What is claimed is:

1. An antibody against varicella-zoster virus comprising a heavy chain variable region comprising the amino acid sequences of HCDR1, HCDR2, and HCDR3, and a light chain variable region comprising the amino acid sequences of LCDR1, LCDR2, and LCDR3, wherein the amino acid sequence of HCDR1 is TYAMH (SEQ ID NO: 45), the amino acid sequence of HCDR2 is VISYGGGNRYYAASVKG (SEQ ID NO: 46), the amino acid sequence of HCDR3 is ARDN-HYFFGMDV (SEQ ID NO: 47), the amino acid sequence of LCDR1 is RASQGISSWLA (SEQ ID NO: 48), the amino acid sequence of LCDR2 is AASSLQS (SEQ ID NO: 49), and the amino acid sequence of LCDR3 is QEGFYFPIN (SEQ ID NO: 51); or the amino acid sequence of HCDR1 is SGNYWN (SEQ ID NO: 29), the amino acid sequence of HCDR2 is YISYDGSTYYNPSLKN (SEQ ID NO: 30), the amino acid sequence of HCDR3 is GYYGYWFAY (SEQ ID NO: 31), the amino acid sequence of LCDR1 is RASSSVSYMH (SEQ ID NO: 32), the amino acid sequence of LCDR2 is ATSNLAS (SEQ ID NO: 33), and the amino acid sequence of LCDR3 is QQWSSNPFT (SEQ ID NO: 34); or the amino acid sequence of HCDR1 is SGYYWN (SEQ ID NO: 54), the amino acid sequence of HCDR2 is YISYDGSNNYNTSLKN (SEQ ID NO: 55), the amino acid sequence of HCDR3 is EDVNYPPYALDY (SEQ ID NO: 35), the amino acid sequence of LCDR1 is RSSQSLVHSNGNTYLH (SEQ ID NO: 36), the amino acid sequence of LCDR2 is KVSNRFS (SEQ ID NO: 37), and the amino acid sequence of LCDR3 is SQSTHVPWT (SEQ ID NO: 38); or the amino acid sequence of HCDR1 is SYTMS (SEQ ID NO: 39), the amino acid sequence of HCDR2 is FISNGGDNNYYADTVKG (SEQ ID NO: 40), the amino acid sequence of HCDR3 is HNGNWGFAY (SEQ ID NO: 41), the amino acid sequence of LCDR1 is SASSSISSNYLH (SEQ ID NO: 42), the amino acid sequence of LCDR2 is RTSNLAS (SEQ ID NO: 43), and the amino acid sequence of LCDR3 is QQGSSIPLT (SEQ ID NO: 44); or the amino acid sequence of HCDR1 is TYAMH (SEQ ID NO: 45), the amino acid sequence of HCDR2 is VISYGGGNRYYAASVKG (SEQ ID NO: 46), the amino acid sequence of HCDR3 is ARDNHYFFGMDV (SEQ ID NO: 47), the amino acid sequence of LCDR1 is RASQGISSWLA (SEQ ID NO: 48), the amino acid sequence of LCDR2 is AASSLQS (SEQ ID NO: 49), and the amino acid sequence of LCDR3 is QQANSFPLT (SEQ ID NO: 50), QQATYFPIN (SEQ ID NO: 52) or QQSSYFPIA (SEQ ID NO: 53);

wherein the amino acid sequences of HCDRs and LCDRs are defined according to Kabat.

2. The antibody of claim 1, wherein the amino acid sequence of the heavy chain variable region of the antibody is set forth in SEQ ID NO: 1, 3, 5, or 7.

3. The antibody of claim 1, wherein the amino acid sequence of the light chain variable region of the antibody is set forth in SEQ ID NO: 2, 4, 6, 8, 9, 10, or 28.

4. The antibody of claim 1, wherein the amino acid sequence of the heavy chain variable region of the antibody is set forth in SEQ ID NO: 1, and the amino acid sequence of the light chain variable region of the antibody is set forth in SEQ ID NO: 2; or the amino acid sequence of the heavy chain variable region of the antibody is set forth in SEQ ID NO: 3, and the amino acid sequence of the light chain variable region of the antibody is set forth in SEQ ID NO: 4; or the amino acid sequence of the heavy chain variable region of the antibody is set forth in SEQ ID NO: 5, and the amino acid sequence of the light chain variable region of the antibody is set forth in SEQ ID NO: 6; or the amino acid sequence of the heavy chain variable region of the antibody is set forth in SEQ ID NO: 7, and the amino acid sequence of the light chain variable region of the antibody is set forth in SEQ ID NO: 8; or the amino acid sequence of the heavy chain variable region of the antibody is set forth in SEQ ID NO: 7, and the amino acid sequence of the light chain variable region of the antibody is set forth in SEQ ID NO: 9; or the amino acid sequence of the heavy chain variable region of the antibody is set forth in SEQ ID NO: 7, and the amino acid sequence of the light chain variable region of the antibody is set forth in SEQ ID NO: 10; or the amino acid sequence of the heavy chain variable region of the antibody is set forth in SEQ ID NO: 7, and the amino acid sequence of the light chain variable region of the antibody is set forth in SEQ ID NO: 28.

5. The antibody of claim 1, wherein the amino acid sequence of the heavy chain variable region of the antibody has at least 90% identity to the amino acid sequence as set forth in any one of SEQ ID NOs: 1, 3, 5, and 7, and the amino acid sequence of the light chain variable region of the antibody has at least 90% identity to the amino acid sequence as set forth in any one of SEQ ID NOs: 2, 4, 6, 8, 9, 10, and 28.

6. The antibody of claim 1, wherein the antibody is a whole antibody, a Fab fragment, a $F(ab')_2$ fragment, or a single chain Fv (scFv).

7. The antibody of claim 1, wherein the antibody is a fully human antibody.

8. The antibody of claim 1, wherein the antibody is a monoclonal antibody.

9. The antibody of claim 1, wherein the antibody further comprises a heavy chain constant region selected from an IgG1 subtype, an IgG2 subtype, or an IgG4 subtype.

10. The antibody of claim 9, wherein the heave chain constant region is an IgG1 subtype.

11. The antibody of claim 1, wherein the antibody further comprises a light chain constant region selected from a kappa subtype or a lamda subtype.

12. The antibody of claim 11, wherein the light chain constant region is a kappa subtype.

13. The antibody of claim 1, wherein the antibody binds to the gH/gL protein of varicella-zoster virus.

14. The antibody of claim 1, wherein the antibody mediates antibody-dependent cell-mediated cytotoxicity (ADCC).

15. A nucleic acid molecule encoding the antibody of claim 1.

16. A pharmaceutical composition comprising the antibody of claim 1 and a pharmaceutically acceptable excipient, diluent or carrier.

17. A method of treating varicella and herpes zoster, comprising administering to a subject in need thereof the antibody of claim 1.

* * * * *